United States Patent
Sekiguchi et al.

(10) Patent No.: US 9,447,167 B2
(45) Date of Patent: Sep. 20, 2016

(54) FIBRINOGEN-PRODUCING TRANSGENIC SILKWORM

(75) Inventors: Satoshi Sekiguchi, Atsugi (JP); Manabu Takahisa, Atsugi (JP); Masahiro Tomita, Fujioka (JP)

(73) Assignee: IMMUNO-BIOLOGICAL LABORATORIES CO., LTD, Fujioka-Shi, Gunma (JP)

( * ) Notice: Subject to any disclaimer, the term of this patent is extended or adjusted under 35 U.S.C. 154(b) by 50 days.

(21) Appl. No.: 14/002,430

(22) PCT Filed: Mar. 2, 2012

(86) PCT No.: PCT/JP2012/055366
§ 371 (c)(1),
(2), (4) Date: Sep. 3, 2013

(87) PCT Pub. No.: WO2012/118176
PCT Pub. Date: Sep. 7, 2012

(65) Prior Publication Data
US 2013/0345401 A1 Dec. 26, 2013

(30) Foreign Application Priority Data
Mar. 3, 2011 (JP) .................. 2011-046386

(51) Int. Cl.
*C12N 15/00* (2006.01)
*C07K 14/75* (2006.01)
*A01K 67/04* (2006.01)

(52) U.S. Cl.
CPC .............. *C07K 14/75* (2013.01); *A01K 67/04* (2013.01); *A01K 2217/052* (2013.01); *A01K 2227/706* (2013.01); *A01K 2267/01* (2013.01)

(58) Field of Classification Search
CPC ............................... A01K 67/04; C07K 14/75
USPC ......................................................... 800/21
See application file for complete search history.

(56) References Cited

U.S. PATENT DOCUMENTS

| | | | |
|---|---|---|---|
| 8,283,137 B2 | 10/2012 | Matsuyama et al. | |
| 2007/0083940 A1 | 4/2007 | Yoshizato et al. | |
| 2008/0301823 A1 | 12/2008 | Tomita et al. | |
| 2011/0203009 A1 | 8/2011 | Tomita et al. | |

FOREIGN PATENT DOCUMENTS

| | | |
|---|---|---|
| EP | 1 391 509 A1 | 2/2004 |
| EP | 1 811 027 A1 | 7/2007 |
| JP | 2001-161214 A | 6/2001 |
| JP | 2002-315580 A | 10/2002 |
| JP | 2004-16144 A | 1/2004 |
| JP | 2006-109772 A | 4/2006 |
| JP | 2009-502166 A | 1/2009 |
| JP | 2009-528843 A | 8/2009 |
| JP | 2009-225781 A | 10/2009 |
| JP | 4573775 B2 | 11/2010 |
| WO | WO 95/22249 | 8/1995 |
| WO | 2004-16055 A | 1/2004 |
| WO | WO 2007/015782 A1 | 2/2007 |
| WO | WO 2007/103447 A2 | 9/2007 |

OTHER PUBLICATIONS

Greenberg et al., (1985, JCI, vol. 75, pp. 1463-1470).*
Redman et al. (2001, Ann. NY Acad. Sci, vol. 936, pp. 480-495).*
Li et al., 2014, J. Chem., Pharm., Res., vol. 6(5), pp. 118-129).*
Subramanian et al., 1997, Biomedical Engineering Conf., Proceedings of the 1997 Sixteenth Southern, pp. 57-60).*
Adachi et al., "Production of a Non-Triple Helical Collagen α Chain in Transgenic Silkworms and Its Evaluation as a Gelatin Substitute for Cell Culture", Biotechnology and Bioengineering, vol. 106, No. 6 (2010) pp. 860-870.
Extended European Search Report issued in European Patent Application No. 12752986.5 on Sep. 24, 2014.
Iizuka et al., "Production of a recombinant mouse monoclonal antibody in transgenic silkworm cocoons", The FEBS Journal, vol. 275 (2009) pp. 5806-5820.
Iizuka et al., "Translational Enhancement of Recombinant Protein Synthesis in Transgenic Silkworms by a 5'-Untranslated Region of Polyhedrin Gene of Bombyx mori Nucleopolyhedrovirus", Journal of Bioscience and Bioengineering, vol. 105, No. 6 (2008) pp. 595-603.
Ogawa et al., "Generation of a transgenic silkworm that secretes recombinant proteins in the sericin layer of cocoon. Production of recombinant human serum albumin", Journal of Biotechnology, vol. 128 (2007) pp. 531-544.
Tatematsu et al., "Construction of a binary transgenic expression system for recombinant protein production in the middle silk gland of the silkworm Bombyx mori", Transgenic Res., vol. 19 (2010) pp. 473-487.
Tomita et al., "A germline transgenic silkworm that secretes recombinant proteins in the sericin layer of cocoon", Transgenic Res., vol. 16 (2007) pp. 449-465.
Tomita. "Transgenic silkworms that weave recombinant proteins into silk cocoons", Biotechnol Lett, vol. 33 (2011) pp. 645-654.
Zhao et al., "New and highly efficient expression systems for expressing selectively foreign protein in the silk glands of transgeneic silkworm", Transgeneic Res., vol. 19 (2010) pp. 29-44.

(Continued)

*Primary Examiner* — Anoop Singh
*Assistant Examiner* — David A Montanari
(74) *Attorney, Agent, or Firm* — Birch, Stewart, Kolasch & Birch, LLP

(57) ABSTRACT

Disclosed is a novel means that enables mass production of highly safe fibrinogen at low cost. The transgenic silkworm of the present invention expresses the fibrinogen subunit Aα, Bβ and γ chains in the silk gland cells and produces fibrinogen having coagulation activity in the cocoon filament. Preferably, the transgenic silkworm expresses the subunits in the middle silk gland cells and produces fibrinogen in the sericin layer of the cocoon filament. By recovering fibrinogen from the cocoon of the transgenic silkworm of the present invention, highly safe fibrinogen can be mass-produced at low cost.

11 Claims, 9 Drawing Sheets

(56) References Cited

OTHER PUBLICATIONS

International Search Report for International Application No. PCT/JP2012/055366 dated May 29, 2012.
Tojo et al., "Recombinant human fibrinogen expressed in the yeast *Pichia pastoris* was assembled and biologically active", Protein Expr Purif, vol. 59, No. 2, Jun. 2008, pp. 289-296 (English Abstract Provided).
Tomita et al., "Production of recombinant fibrinogen using transgenic silkworm", Japan Society for Bioscience, Biotechnology and Agrochemistry, vol. 2011, Mar. 5, 2011, p. 294 (with English translation).

* cited by examiner

SEQUENCE LISTING

<160> NUMBER OF SEQ ID NOS: 34

<210> SEQ ID NO 1
<211> LENGTH: 2210
<212> TYPE: DNA
<213> ORGANISM: Homo sapiens
<220> FEATURE:
<221> NAME/KEY: CDS
<222> LOCATION: (59)..(1993)
<223> OTHER INFORMATION:

<400> SEQUENCE: 1

```
agcaatcctt tctttcagct ggagtgctcc tcaggagcca gccccaccct tagaaaag          58 atg ttt tcc atg agg atc gtc tgc ctg gtc cta agt gtg gtg ggc aca        106
Met Phe Ser Met Arg Ile Val Cys Leu Val Leu Ser Val Val Gly Thr
1               5                   10                  15 gca tgg act gca gat agt ggt gaa ggt gac ttt cta gct gaa gga gga        154
Ala Trp Thr Ala Asp Ser Gly Glu Gly Asp Phe Leu Ala Glu Gly Gly
                20                  25                  30 ggc gtg cgt ggc cca agg gtt gtg gaa aga cat caa tct gcc tgc aaa        202
Gly Val Arg Gly Pro Arg Val Val Glu Arg His Gln Ser Ala Cys Lys
            35                  40                  45 gat tca gac tgg ccc ttc tgc tct gat gaa gac tgg aac tac aaa tgc        250
Asp Ser Asp Trp Pro Phe Cys Ser Asp Glu Asp Trp Asn Tyr Lys Cys
        50                  55                  60 cct tct ggc tgc agg atg aaa ggg ttg att gat gaa gtc aat caa gat        298
Pro Ser Gly Cys Arg Met Lys Gly Leu Ile Asp Glu Val Asn Gln Asp
65                  70                  75                  80 ttt aca aac aga ata aat aag ctc aaa aat tca cta ttt gaa tat cag        346
Phe Thr Asn Arg Ile Asn Lys Leu Lys Asn Ser Leu Phe Glu Tyr Gln
                85                  90                  95 aag aac aat aag gat tct cat tcg ttg acc act aat ata atg gaa att        394
Lys Asn Asn Lys Asp Ser His Ser Leu Thr Thr Asn Ile Met Glu Ile
```

|  |  |  |  |  |  |  |  |  |  |  |  |  |  |  |  |
|---|---|---|---|---|---|---|---|---|---|---|---|---|---|---|---|
|  |  | 100 |  |  |  | 105 |  |  |  | 110 |  |  |  |  |  |
| ttg | aga | ggc | gat | ttt | tcc | tca | gcc | aat | aac | cgt | gat | aat | acc | tac | aac | 442 |
| Leu | Arg | Gly | Asp | Phe | Ser | Ser | Ala | Asn | Asn | Arg | Asp | Asn | Thr | Tyr | Asn |  |
|  |  | 115 |  |  |  | 120 |  |  |  | 125 |  |  |  |  |  |
| cga | gtg | tca | gag | gat | ctg | aga | agc | aga | att | gaa | gtc | ctg | aag | cgc | aaa | 490 |
| Arg | Val | Ser | Glu | Asp | Leu | Arg | Ser | Arg | Ile | Glu | Val | Leu | Lys | Arg | Lys |  |
|  | 130 |  |  |  |  | 135 |  |  |  |  | 140 |  |  |  |  |
| gtc | ata | gaa | aaa | gta | cag | cat | atc | cag | ctt | ctg | cag | aaa | aat | gtt | aga | 538 |
| Val | Ile | Glu | Lys | Val | Gln | His | Ile | Gln | Leu | Leu | Gln | Lys | Asn | Val | Arg |  |
| 145 |  |  |  |  | 150 |  |  |  |  | 155 |  |  |  |  | 160 |
| gct | cag | ttg | gtt | gat | atg | aaa | cga | ctg | gag | gtg | gac | att | gat | att | aag | 586 |
| Ala | Gln | Leu | Val | Asp | Met | Lys | Arg | Leu | Glu | Val | Asp | Ile | Asp | Ile | Lys |  |
|  |  |  |  | 165 |  |  |  |  | 170 |  |  |  |  | 175 |  |
| atc | cga | tct | tgt | cga | ggg | tca | tgc | agt | agg | gct | tta | gct | cgt | gaa | gta | 634 |
| Ile | Arg | Ser | Cys | Arg | Gly | Ser | Cys | Ser | Arg | Ala | Leu | Ala | Arg | Glu | Val |  |
|  |  |  | 180 |  |  |  |  | 185 |  |  |  |  | 190 |  |  |
| gat | ctg | aag | gac | tat | gaa | gat | cag | cag | aag | caa | ctt | gaa | cag | gtc | att | 682 |
| Asp | Leu | Lys | Asp | Tyr | Glu | Asp | Gln | Gln | Lys | Gln | Leu | Glu | Gln | Val | Ile |  |
|  |  | 195 |  |  |  | 200 |  |  |  | 205 |  |  |  |  |  |
| gcc | aaa | gac | tta | ctt | ccc | tct | aga | gat | agg | caa | cac | tta | cca | ctg | ata | 730 |
| Ala | Lys | Asp | Leu | Leu | Pro | Ser | Arg | Asp | Arg | Gln | His | Leu | Pro | Leu | Ile |  |
|  | 210 |  |  |  |  | 215 |  |  |  |  | 220 |  |  |  |  |
| aaa | atg | aaa | cca | gtt | cca | gac | ttg | gtt | ccc | gga | aat | ttt | aag | agc | cag | 778 |
| Lys | Met | Lys | Pro | Val | Pro | Asp | Leu | Val | Pro | Gly | Asn | Phe | Lys | Ser | Gln |  |
| 225 |  |  |  |  | 230 |  |  |  |  | 235 |  |  |  |  | 240 |
| ctt | cag | aag | gta | ccc | cca | gag | tgg | aag | gca | tta | aca | gac | atg | ccg | cag | 826 |
| Leu | Gln | Lys | Val | Pro | Pro | Glu | Trp | Lys | Ala | Leu | Thr | Asp | Met | Pro | Gln |  |
|  |  |  |  | 245 |  |  |  |  | 250 |  |  |  |  | 255 |  |
| atg | aga | atg | gag | tta | gag | aga | cct | ggt | gga | aat | gag | att | act | cga | gga | 874 |
| Met | Arg | Met | Glu | Leu | Glu | Arg | Pro | Gly | Gly | Asn | Glu | Ile | Thr | Arg | Gly |  |
|  |  |  | 260 |  |  |  |  | 265 |  |  |  |  | 270 |  |  |
| ggc | tcc | acc | tct | tat | gga | acc | gga | tca | gag | acg | gaa | agc | ccc | agg | aac | 922 |
| Gly | Ser | Thr | Ser | Tyr | Gly | Thr | Gly | Ser | Glu | Thr | Glu | Ser | Pro | Arg | Asn |  |
|  |  | 275 |  |  |  | 280 |  |  |  | 285 |  |  |  |  |  |
| cct | agc | agt | gct | gga | agc | tgg | aac | tct | ggg | agc | tct | gga | cct | gga | agt | 970 |
| Pro | Ser | Ser | Ala | Gly | Ser | Trp | Asn | Ser | Gly | Ser | Ser | Gly | Pro | Gly | Ser |  |
|  | 290 |  |  |  |  | 295 |  |  |  |  | 300 |  |  |  |  |
| act | gga | aac | cga | aac | cct | ggg | agc | tct | ggg | act | gga | ggg | act | gca | acc | 1018 |
| Thr | Gly | Asn | Arg | Asn | Pro | Gly | Ser | Ser | Gly | Thr | Gly | Gly | Thr | Ala | Thr |  |
| 305 |  |  |  |  | 310 |  |  |  |  | 315 |  |  |  |  | 320 |
| tgg | aaa | cct | ggg | agc | tct | gga | cct | gga | agt | act | gga | agc | tgg | aac | tct | 1066 |
| Trp | Lys | Pro | Gly | Ser | Ser | Gly | Pro | Gly | Ser | Thr | Gly | Ser | Trp | Asn | Ser |  |
|  |  |  |  | 325 |  |  |  |  | 330 |  |  |  |  | 335 |  |
| ggg | agc | tct | gga | act | gga | agt | act | gga | aac | caa | aac | cct | ggg | agc | cct | 1114 |
| Gly | Ser | Ser | Gly | Thr | Gly | Ser | Thr | Gly | Asn | Gln | Asn | Pro | Gly | Ser | Pro |  |
|  |  |  | 340 |  |  |  |  | 345 |  |  |  |  | 350 |  |  |
| aga | cct | ggt | agt | acc | gga | acc | tgg | aat | cct | ggc | agc | tct | gaa | cgc | gga | 1162 |
| Arg | Pro | Gly | Ser | Thr | Gly | Thr | Trp | Asn | Pro | Gly | Ser | Ser | Glu | Arg | Gly |  |
|  |  | 355 |  |  |  | 360 |  |  |  | 365 |  |  |  |  |  |
| agt | gct | ggg | cac | tgg | acc | tct | gag | agc | tct | gta | tct | ggt | agt | act | gga | 1210 |
| Ser | Ala | Gly | His | Trp | Thr | Ser | Glu | Ser | Ser | Val | Ser | Gly | Ser | Thr | Gly |  |
|  | 370 |  |  |  |  | 375 |  |  |  |  | 380 |  |  |  |  |
| caa | tgg | cac | tct | gaa | tct | gga | agt | ttt | agg | cca | gat | agc | cca | ggc | tct | 1258 |
| Gln | Trp | His | Ser | Glu | Ser | Gly | Ser | Phe | Arg | Pro | Asp | Ser | Pro | Gly | Ser |  |
| 385 |  |  |  |  | 390 |  |  |  |  | 395 |  |  |  |  | 400 |
| ggg | aac | gcg | agg | cct | aac | aac | cca | gac | tgg | ggc | aca | ttt | gaa | gag | gtg | 1306 |
| Gly | Asn | Ala | Arg | Pro | Asn | Asn | Pro | Asp | Trp | Gly | Thr | Phe | Glu | Glu | Val |  |
|  |  |  |  | 405 |  |  |  |  | 410 |  |  |  |  | 415 |  |
| tca | gga | aat | gta | agt | cca | ggg | aca | agg | aga | gag | tac | cac | aca | gaa | aaa | 1354 |

```
Ser Gly Asn Val Ser Pro Gly Thr Arg Arg Glu Tyr His Thr Glu Lys
            420                 425                 430 ctg gtc act tct aaa gga gat aaa gag ctc agg act ggt aaa gag aag         1402
Leu Val Thr Ser Lys Gly Asp Lys Glu Leu Arg Thr Gly Lys Glu Lys
        435                 440                 445 gtc acc tct ggt agc aca acc acc acg cgt cgt tca tgc tct aaa acc         1450
Val Thr Ser Gly Ser Thr Thr Thr Thr Arg Arg Ser Cys Ser Lys Thr
    450                 455                 460 gtt act aag act gtt att ggt cct gat ggt cac aaa gaa gtt acc aaa         1498
Val Thr Lys Thr Val Ile Gly Pro Asp Gly His Lys Glu Val Thr Lys
465                 470                 475                 480 gaa gtg gtg acc tcc gaa gat ggt tct gac tgt ccc gag gca atg gat         1546
Glu Val Val Thr Ser Glu Asp Gly Ser Asp Cys Pro Glu Ala Met Asp
                485                 490                 495 tta ggc aca ttg tct ggc ata ggt act ctg gat ggg ttc cgc cat agg         1594
Leu Gly Thr Leu Ser Gly Ile Gly Thr Leu Asp Gly Phe Arg His Arg
            500                 505                 510 cac cct gat gaa gct gcc ttc ttc gac act gcc tca act gga aaa aca         1642
His Pro Asp Glu Ala Ala Phe Phe Asp Thr Ala Ser Thr Gly Lys Thr
        515                 520                 525 ttc cca ggt ttc ttc tca cct atg tta gga gag ttt gtc agt gag act         1690
Phe Pro Gly Phe Phe Ser Pro Met Leu Gly Glu Phe Val Ser Glu Thr
530                 535                 540 gag tct agg ggc tca gaa tct ggc atc ttc aca aat aca aag gaa tcc         1738
Glu Ser Arg Gly Ser Glu Ser Gly Ile Phe Thr Asn Thr Lys Glu Ser
545                 550                 555                 560 agt tct cat cac cct ggg ata gct gaa ttc cct tcc cgt ggt aaa tct         1786
Ser Ser His His Pro Gly Ile Ala Glu Phe Pro Ser Arg Gly Lys Ser
                565                 570                 575 tca agt tac agc aaa caa ttt act agt agc acg agt tac aac aga gga         1834
Ser Ser Tyr Ser Lys Gln Phe Thr Ser Ser Thr Ser Tyr Asn Arg Gly
            580                 585                 590 gac tcc aca ttt gaa agc aag agc tat aaa atg gca gat gag gcc gga         1882
Asp Ser Thr Phe Glu Ser Lys Ser Tyr Lys Met Ala Asp Glu Ala Gly
        595                 600                 605 agt gaa gcc gat cat gaa gga aca cat agc acc aag aga ggc cat gct         1930
Ser Glu Ala Asp His Glu Gly Thr His Ser Thr Lys Arg Gly His Ala
610                 615                 620 aaa tct cgc cct gtc aga ggt atc cac act tct cct ttg ggg aag cct         1978
Lys Ser Arg Pro Val Arg Gly Ile His Thr Ser Pro Leu Gly Lys Pro
625                 630                 635                 640 tcc ctg tcc ccc tag actaagttaa atatttctgc acagtgttcc catggcccct         2033
Ser Leu Ser Pro tgcatttcct tcttaactct ctgttacacg tcattgaaac tacactttt tggtctgttt        2093 ttgtgctaga ctgtaagttc cttgggggca gggcctttgt ctgtctcatc tctgtattcc       2153
caaatgccta acagtacaga gccatgactc aataaataca tgttaaatgg atgaatg          2210

<210> SEQ ID NO 2
<211> LENGTH: 644
<212> TYPE: PRT
<213> ORGANISM: Homo sapiens

<400> SEQUENCE: 2

Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
            20                  25                  30

Gly Val Arg Gly Pro Arg Val Val Glu Arg His Gln Ser Ala Cys Lys
```

```
                35                  40                  45
Asp Ser Asp Trp Pro Phe Cys Ser Asp Glu Asp Trp Asn Tyr Lys Cys
 50                  55                  60

Pro Ser Gly Cys Arg Met Lys Gly Leu Ile Asp Glu Val Asn Gln Asp
 65                  70                  75                  80

Phe Thr Asn Arg Ile Asn Lys Leu Lys Asn Ser Leu Phe Glu Tyr Gln
                     85                  90                  95

Lys Asn Asn Lys Asp Ser His Ser Leu Thr Thr Asn Ile Met Glu Ile
                100                 105                 110

Leu Arg Gly Asp Phe Ser Ser Ala Asn Asn Arg Asp Asn Thr Tyr Asn
                115                 120                 125

Arg Val Ser Glu Asp Leu Arg Ser Arg Ile Glu Val Leu Lys Arg Lys
                130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
                180                 185                 190

Asp Leu Lys Asp Tyr Glu Asp Gln Gln Lys Gln Leu Glu Gln Val Ile
                195                 200                 205

Ala Lys Asp Leu Leu Pro Ser Arg Asp Arg Gln His Leu Pro Leu Ile
                210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
                260                 265                 270

Gly Ser Thr Ser Tyr Gly Thr Gly Ser Glu Thr Glu Ser Pro Arg Asn
                275                 280                 285

Pro Ser Ser Ala Gly Ser Trp Asn Ser Gly Ser Ser Gly Pro Gly Ser
                290                 295                 300

Thr Gly Asn Arg Asn Pro Gly Ser Ser Gly Thr Gly Gly Thr Ala Thr
305                 310                 315                 320

Trp Lys Pro Gly Ser Ser Gly Pro Gly Ser Thr Gly Ser Trp Asn Ser
                325                 330                 335

Gly Ser Ser Gly Thr Gly Ser Thr Gly Asn Gln Asn Pro Gly Ser Pro
                340                 345                 350

Arg Pro Gly Ser Thr Gly Thr Trp Asn Pro Gly Ser Ser Glu Arg Gly
                355                 360                 365

Ser Ala Gly His Trp Thr Ser Glu Ser Ser Val Ser Gly Ser Thr Gly
                370                 375                 380

Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
                405                 410                 415

Ser Gly Asn Val Ser Pro Gly Thr Arg Arg Glu Tyr His Thr Glu Lys
                420                 425                 430

Leu Val Thr Ser Lys Gly Asp Lys Glu Leu Arg Thr Gly Lys Glu Lys
                435                 440                 445

Val Thr Ser Gly Ser Thr Thr Thr Thr Arg Arg Ser Cys Ser Lys Thr
450                 455                 460
```

```
Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
                485                 490                 495

Leu Gly Thr Leu Ser Gly Ile Gly Thr Leu Asp Gly Phe Arg His Arg
            500                 505                 510

His Pro Asp Glu Ala Ala Phe Phe Asp Thr Ala Ser Thr Gly Lys Thr
            515                 520                 525

Phe Pro Gly Phe Phe Ser Pro Met Leu Gly Glu Phe Val Ser Glu Thr
    530                 535                 540

Glu Ser Arg Gly Ser Glu Ser Gly Ile Phe Thr Asn Thr Lys Glu Ser
545                 550                 555                 560

Ser Ser His His Pro Gly Ile Ala Glu Phe Pro Ser Arg Gly Lys Ser
                565                 570                 575

Ser Ser Tyr Ser Lys Gln Phe Thr Ser Ser Thr Ser Tyr Asn Arg Gly
            580                 585                 590

Asp Ser Thr Phe Glu Ser Lys Ser Tyr Lys Met Ala Asp Glu Ala Gly
            595                 600                 605

Ser Glu Ala Asp His Glu Gly Thr His Ser Thr Lys Arg Gly His Ala
    610                 615                 620

Lys Ser Arg Pro Val Arg Gly Ile His Thr Ser Pro Leu Gly Lys Pro
625                 630                 635                 640

Ser Leu Ser Pro

<210> SEQ ID NO 3
<211> LENGTH: 1950
<212> TYPE: DNA
<213> ORGANISM: Artificial
<220> FEATURE:
<223> OTHER INFORMATION: human fibrinogen A alpha insert cDNA
<220> FEATURE:
<221> NAME/KEY: CDS
<222> LOCATION: (61)..(1944)
<223> OTHER INFORMATION:

<400> SEQUENCE: 3
caccccgggg aagtatttta ctgttttcgt aacagttttg taataaaaaa acctataaat      60 atg ctg cta tcc gtg ccg ttg ctg ctc ggc ctc ctc ggc ctg gcc gtc     108
Met Leu Leu Ser Val Pro Leu Leu Leu Gly Leu Leu Gly Leu Ala Val
1               5                   10                  15 gcc gca gat agt ggt gaa ggt gac ttt cta gct gaa gga gga ggc gtg     156
Ala Ala Asp Ser Gly Glu Gly Asp Phe Leu Ala Glu Gly Gly Gly Val
            20                  25                  30 cgt ggc cca agg gtt gtg gaa aga cat caa tct gcc tgc aaa gat tca     204
Arg Gly Pro Arg Val Val Glu Arg His Gln Ser Ala Cys Lys Asp Ser
        35                  40                  45 gac tgg ccc ttc tgc tct gat gaa gac tgg aac tac aaa tgc cct tct     252
Asp Trp Pro Phe Cys Ser Asp Glu Asp Trp Asn Tyr Lys Cys Pro Ser
    50                  55                  60 ggc tgc agg atg aaa ggg ttg att gat gaa gtc aat caa gat ttt aca     300
Gly Cys Arg Met Lys Gly Leu Ile Asp Glu Val Asn Gln Asp Phe Thr
65                  70                  75                  80 aac aga ata aat aag ctc aaa aat tca cta ttt gaa tat cag aag aac     348
Asn Arg Ile Asn Lys Leu Lys Asn Ser Leu Phe Glu Tyr Gln Lys Asn
                85                  90                  95 aat aag gat tct cat tcg ttg acc act aat ata atg gaa att ttg aga     396
Asn Lys Asp Ser His Ser Leu Thr Thr Asn Ile Met Glu Ile Leu Arg
            100                 105                 110
```

| | | | | | | | | | | | | | | | | |
|---|---|---|---|---|---|---|---|---|---|---|---|---|---|---|---|---|
| ggc | gat | ttt | tcc | tca | gcc | aat | aac | cgt | gat | aat | acc | tac | aac | cga | gtg | 444 |
| Gly | Asp | Phe | Ser | Ser | Ala | Asn | Asn | Arg | Asp | Asn | Thr | Tyr | Asn | Arg | Val | |
| | | 115 | | | | 120 | | | | | 125 | | | | | |
| tca | gag | gat | ctg | aga | agc | aga | att | gaa | gtc | ctg | aag | cgc | aaa | gtc | ata | 492 |
| Ser | Glu | Asp | Leu | Arg | Ser | Arg | Ile | Glu | Val | Leu | Lys | Arg | Lys | Val | Ile | |
| 130 | | | | | 135 | | | | | 140 | | | | | | |
| gaa | aaa | gta | cag | cat | atc | cag | ctt | ctg | cag | aaa | aat | gtt | aga | gct | cag | 540 |
| Glu | Lys | Val | Gln | His | Ile | Gln | Leu | Leu | Gln | Lys | Asn | Val | Arg | Ala | Gln | |
| 145 | | | | 150 | | | | | 155 | | | | | | 160 | |
| ttg | gtt | gat | atg | aaa | cga | ctg | gag | gtg | gac | att | gat | att | aag | atc | cga | 588 |
| Leu | Val | Asp | Met | Lys | Arg | Leu | Glu | Val | Asp | Ile | Asp | Ile | Lys | Ile | Arg | |
| | | | | 165 | | | | | 170 | | | | | 175 | | |
| tct | tgt | cga | ggg | tca | tgc | agt | agg | gct | tta | gct | cgt | gaa | gta | gat | ctg | 636 |
| Ser | Cys | Arg | Gly | Ser | Cys | Ser | Arg | Ala | Leu | Ala | Arg | Glu | Val | Asp | Leu | |
| | | 180 | | | | 185 | | | | | 190 | | | | | |
| aag | gac | tat | gaa | gat | cag | cag | aag | caa | ctt | gaa | cag | gtc | att | gcc | aaa | 684 |
| Lys | Asp | Tyr | Glu | Asp | Gln | Gln | Lys | Gln | Leu | Glu | Gln | Val | Ile | Ala | Lys | |
| | | 195 | | | | 200 | | | | | 205 | | | | | |
| gac | tta | ctt | ccc | tct | aga | gat | agg | caa | cac | tta | cca | ctg | ata | aaa | atg | 732 |
| Asp | Leu | Leu | Pro | Ser | Arg | Asp | Arg | Gln | His | Leu | Pro | Leu | Ile | Lys | Met | |
| | 210 | | | | | 215 | | | | | 220 | | | | | |
| aaa | cca | gtt | cca | gac | ttg | gtt | ccc | gga | aat | ttt | aag | agc | cag | ctt | cag | 780 |
| Lys | Pro | Val | Pro | Asp | Leu | Val | Pro | Gly | Asn | Phe | Lys | Ser | Gln | Leu | Gln | |
| 225 | | | | | 230 | | | | | 235 | | | | | 240 | |
| aag | gta | ccc | cca | gag | tgg | aag | gca | tta | aca | gac | atg | ccg | cag | atg | aga | 828 |
| Lys | Val | Pro | Pro | Glu | Trp | Lys | Ala | Leu | Thr | Asp | Met | Pro | Gln | Met | Arg | |
| | | | | 245 | | | | | 250 | | | | | 255 | | |
| atg | gag | tta | gag | aga | cct | ggt | gga | aat | gag | att | act | cga | gga | ggc | tcc | 876 |
| Met | Glu | Leu | Glu | Arg | Pro | Gly | Gly | Asn | Glu | Ile | Thr | Arg | Gly | Gly | Ser | |
| | | | 260 | | | | | 265 | | | | | 270 | | | |
| acc | tct | tat | gga | acc | gga | tca | gag | acg | gaa | agc | ccc | agg | aac | cct | agc | 924 |
| Thr | Ser | Tyr | Gly | Thr | Gly | Ser | Glu | Thr | Glu | Ser | Pro | Arg | Asn | Pro | Ser | |
| | | 275 | | | | 280 | | | | | 285 | | | | | |
| agt | gct | gga | agc | tgg | aac | tct | ggg | agc | tct | gga | cct | gga | agt | act | gga | 972 |
| Ser | Ala | Gly | Ser | Trp | Asn | Ser | Gly | Ser | Ser | Gly | Pro | Gly | Ser | Thr | Gly | |
| | 290 | | | | | 295 | | | | | 300 | | | | | |
| aac | cga | aac | cct | ggg | agc | tct | ggg | act | gga | ggg | act | gca | acc | tgg | aaa | 1020 |
| Asn | Arg | Asn | Pro | Gly | Ser | Ser | Gly | Thr | Gly | Gly | Thr | Ala | Thr | Trp | Lys | |
| 305 | | | | | 310 | | | | | 315 | | | | | 320 | |
| cct | ggg | agc | tct | gga | cct | gga | agt | act | gga | agc | tgg | aac | tct | ggg | agc | 1068 |
| Pro | Gly | Ser | Ser | Gly | Pro | Gly | Ser | Thr | Gly | Ser | Trp | Asn | Ser | Gly | Ser | |
| | | | 325 | | | | | 330 | | | | | 335 | | | |
| tct | gga | act | gga | agt | act | gga | aac | caa | aac | cct | ggg | agc | cct | aga | cct | 1116 |
| Ser | Gly | Thr | Gly | Ser | Thr | Gly | Asn | Gln | Asn | Pro | Gly | Ser | Pro | Arg | Pro | |
| | | | 340 | | | | | 345 | | | | | 350 | | | |
| ggt | agt | acc | gga | acc | tgg | aat | cct | ggc | agc | tct | gaa | cgc | gga | agt | gct | 1164 |
| Gly | Ser | Thr | Gly | Thr | Trp | Asn | Pro | Gly | Ser | Ser | Glu | Arg | Gly | Ser | Ala | |
| | | 355 | | | | 360 | | | | | 365 | | | | | |
| ggg | cac | tgg | acc | tct | gag | agc | tct | gta | tct | ggt | agt | act | gga | caa | tgg | 1212 |
| Gly | His | Trp | Thr | Ser | Glu | Ser | Ser | Val | Ser | Gly | Ser | Thr | Gly | Gln | Trp | |
| | 370 | | | | | 375 | | | | | 380 | | | | | |
| cac | tct | gaa | tct | gga | agt | ttt | agg | cca | gat | agc | cca | ggc | tct | ggg | aac | 1260 |
| His | Ser | Glu | Ser | Gly | Ser | Phe | Arg | Pro | Asp | Ser | Pro | Gly | Ser | Gly | Asn | |
| 385 | | | | | 390 | | | | | 395 | | | | | 400 | |
| gcg | agg | cct | aac | aac | cca | gac | tgg | ggc | aca | ttt | gaa | gag | gtg | tca | gga | 1308 |
| Ala | Arg | Pro | Asn | Asn | Pro | Asp | Trp | Gly | Thr | Phe | Glu | Glu | Val | Ser | Gly | |
| | | | | 405 | | | | | 410 | | | | | 415 | | |
| aat | gta | agt | cca | ggg | aca | agg | aga | gag | tac | cac | aca | gaa | aaa | ctg | gtc | 1356 |
| Asn | Val | Ser | Pro | Gly | Thr | Arg | Arg | Glu | Tyr | His | Thr | Glu | Lys | Leu | Val | |

```
               420             425             430
act tct aaa gga gat aaa gag ctc agg act ggt aaa gag aag gtc acc    1404
Thr Ser Lys Gly Asp Lys Glu Leu Arg Thr Gly Lys Glu Lys Val Thr
        435             440             445 tct ggt agc aca acc acc acg cgt cgt tca tgc tct aaa acc gtt act    1452
Ser Gly Ser Thr Thr Thr Thr Arg Arg Ser Cys Ser Lys Thr Val Thr
450             455             460 aag act gtt att ggt cct gat ggt cac aaa gaa gtt acc aaa gaa gtg    1500
Lys Thr Val Ile Gly Pro Asp Gly His Lys Glu Val Thr Lys Glu Val
465             470             475             480 gtg acc tcc gaa gat ggt tct gac tgt ccc gag gca atg gat tta ggc    1548
Val Thr Ser Glu Asp Gly Ser Asp Cys Pro Glu Ala Met Asp Leu Gly
            485             490             495 aca ttg tct ggc ata ggt act ctg gat ggg ttc cgc cat agg cac cct    1596
Thr Leu Ser Gly Ile Gly Thr Leu Asp Gly Phe Arg His Arg His Pro
        500             505             510 gat gaa gct gcc ttc ttc gac act gcc tca act gga aaa aca ttc cca    1644
Asp Glu Ala Ala Phe Phe Asp Thr Ala Ser Thr Gly Lys Thr Phe Pro
        515             520             525 ggt ttc ttc tca cct atg tta gga gag ttt gtc agt gag act gag tct    1692
Gly Phe Phe Ser Pro Met Leu Gly Glu Phe Val Ser Glu Thr Glu Ser
530             535             540 agg ggc tca gaa tct ggc atc ttc aca aat aca aag gaa tcc agt tct    1740
Arg Gly Ser Glu Ser Gly Ile Phe Thr Asn Thr Lys Glu Ser Ser Ser
545             550             555             560 cat cac cct ggg ata gct gaa ttc cct tcc cgt ggt aaa tct tca agt    1788
His His Pro Gly Ile Ala Glu Phe Pro Ser Arg Gly Lys Ser Ser Ser
            565             570             575 tac agc aaa caa ttt act agt agc acg agt tac aac aga gga gac tcc    1836
Tyr Ser Lys Gln Phe Thr Ser Ser Thr Ser Tyr Asn Arg Gly Asp Ser
        580             585             590 aca ttt gaa agc aag agc tat aaa atg gca gat gag gcc gga agt gaa    1884
Thr Phe Glu Ser Lys Ser Tyr Lys Met Ala Asp Glu Ala Gly Ser Glu
        595             600             605 gcc gat cat gaa gga aca cat agc acc aag aga ggc cat gct aaa tct    1932
Ala Asp His Glu Gly Thr His Ser Thr Lys Arg Gly His Ala Lys Ser
610             615             620 cgc cct gtc taa cccggg                                             1950
Arg Pro Val
625

<210> SEQ ID NO 4
<211> LENGTH: 627
<212> TYPE: PRT
<213> ORGANISM: Artificial
<220> FEATURE:
<223> OTHER INFORMATION: human fibrinogen A alpha insert cDNA

<400> SEQUENCE: 4

Met Leu Leu Ser Val Pro Leu Leu Gly Leu Leu Gly Leu Ala Val
1               5                   10                  15

Ala Ala Asp Ser Gly Glu Gly Asp Phe Leu Ala Glu Gly Gly Val
                20                  25                  30

Arg Gly Pro Arg Val Val Glu Arg His Gln Ser Ala Cys Lys Asp Ser
            35                  40                  45

Asp Trp Pro Phe Cys Ser Asp Glu Asp Trp Asn Tyr Lys Cys Pro Ser
        50                  55                  60

Gly Cys Arg Met Lys Gly Leu Ile Asp Glu Val Asn Gln Asp Phe Thr
65                  70                  75                  80
```

```
Asn Arg Ile Asn Lys Leu Lys Asn Ser Leu Phe Glu Tyr Gln Lys Asn
                85                  90                  95
Asn Lys Asp Ser His Ser Leu Thr Thr Asn Ile Met Glu Ile Leu Arg
            100                 105                 110
Gly Asp Phe Ser Ser Ala Asn Asn Arg Asp Asn Thr Tyr Asn Arg Val
            115                 120                 125
Ser Glu Asp Leu Arg Ser Arg Ile Glu Val Leu Lys Arg Lys Val Ile
        130                 135                 140
Glu Lys Val Gln His Ile Gln Leu Leu Gln Lys Asn Val Arg Ala Gln
145                 150                 155                 160
Leu Val Asp Met Lys Arg Leu Glu Val Asp Ile Asp Ile Lys Ile Arg
                165                 170                 175
Ser Cys Arg Gly Ser Cys Ser Arg Ala Leu Ala Arg Glu Val Asp Leu
            180                 185                 190
Lys Asp Tyr Glu Asp Gln Gln Lys Gln Leu Glu Gln Val Ile Ala Lys
            195                 200                 205
Asp Leu Leu Pro Ser Arg Asp Arg Gln His Leu Pro Leu Ile Lys Met
        210                 215                 220
Lys Pro Val Pro Asp Leu Val Pro Gly Asn Phe Lys Ser Gln Leu Gln
225                 230                 235                 240
Lys Val Pro Pro Glu Trp Lys Ala Leu Thr Asp Met Pro Gln Met Arg
                245                 250                 255
Met Glu Leu Glu Arg Pro Gly Gly Asn Glu Ile Thr Arg Gly Gly Ser
            260                 265                 270
Thr Ser Tyr Gly Thr Gly Ser Glu Thr Glu Ser Pro Arg Asn Pro Ser
            275                 280                 285
Ser Ala Gly Ser Trp Asn Ser Gly Ser Ser Gly Pro Gly Ser Thr Gly
        290                 295                 300
Asn Arg Asn Pro Gly Ser Ser Gly Thr Gly Gly Thr Ala Thr Trp Lys
305                 310                 315                 320
Pro Gly Ser Ser Gly Pro Gly Ser Thr Gly Ser Trp Asn Ser Gly Ser
                325                 330                 335
Ser Gly Thr Gly Ser Thr Gly Asn Gln Asn Pro Gly Ser Pro Arg Pro
            340                 345                 350
Gly Ser Thr Gly Thr Trp Asn Pro Gly Ser Ser Glu Arg Gly Ser Ala
            355                 360                 365
Gly His Trp Thr Ser Glu Ser Ser Val Ser Gly Ser Thr Gly Gln Trp
        370                 375                 380
His Ser Glu Ser Gly Ser Phe Arg Pro Asp Ser Pro Gly Ser Gly Asn
385                 390                 395                 400
Ala Arg Pro Asn Asn Pro Asp Trp Gly Thr Phe Glu Glu Val Ser Gly
                405                 410                 415
Asn Val Ser Pro Gly Thr Arg Arg Glu Tyr His Thr Glu Lys Leu Val
            420                 425                 430
Thr Ser Lys Gly Asp Lys Glu Leu Arg Thr Gly Lys Glu Lys Val Thr
            435                 440                 445
Ser Gly Ser Thr Thr Thr Thr Arg Arg Ser Cys Ser Lys Thr Val Thr
        450                 455                 460
Lys Thr Val Ile Gly Pro Asp Gly His Lys Glu Val Thr Lys Glu Val
465                 470                 475                 480
Val Thr Ser Glu Asp Gly Ser Asp Cys Pro Glu Ala Met Asp Leu Gly
                485                 490                 495
Thr Leu Ser Gly Ile Gly Thr Leu Asp Gly Phe Arg His Arg His Pro
```

```
                500                 505                 510
Asp Glu Ala Ala Phe Phe Asp Thr Ala Ser Thr Gly Lys Thr Phe Pro
            515                 520                 525

Gly Phe Phe Ser Pro Met Leu Gly Glu Phe Val Ser Glu Thr Glu Ser
            530                 535                 540

Arg Gly Ser Glu Ser Gly Ile Phe Thr Asn Thr Lys Glu Ser Ser Ser
545                 550                 555                 560

His His Pro Gly Ile Ala Glu Phe Pro Ser Arg Gly Lys Ser Ser Ser
            565                 570                 575

Tyr Ser Lys Gln Phe Thr Ser Ser Thr Ser Tyr Asn Arg Gly Asp Ser
            580                 585                 590

Thr Phe Glu Ser Lys Ser Tyr Lys Met Ala Asp Glu Ala Gly Ser Glu
            595                 600                 605

Ala Asp His Glu Gly Thr His Ser Thr Lys Arg Gly His Ala Lys Ser
            610                 615                 620

Arg Pro Val
625

<210> SEQ ID NO 5
<211> LENGTH: 3628
<212> TYPE: DNA
<213> ORGANISM: Homo sapiens
<220> FEATURE:
<221> NAME/KEY: CDS
<222> LOCATION: (40)..(1515)
<223> OTHER INFORMATION:

<400> SEQUENCE: 5
agatatatat aggattgaag atctctcagt taagtctac atg aaa agg atg gtt         54
                                            Met Lys Arg Met Val
                                            1               5 tct tgg agc ttc cac aaa ctt aaa acc atg aaa cat cta tta ttg cta      102
Ser Trp Ser Phe His Lys Leu Lys Thr Met Lys His Leu Leu Leu Leu
                10                  15                  20 cta ttg tgt gtt ttt cta gtt aag tcc caa ggt gtc aac gac aat gag      150
Leu Leu Cys Val Phe Leu Val Lys Ser Gln Gly Val Asn Asp Asn Glu
            25                  30                  35 gag ggt ttc ttc agt gcc cgt ggt cat cga ccc ctt gac aag aag aga      198
Glu Gly Phe Phe Ser Ala Arg Gly His Arg Pro Leu Asp Lys Lys Arg
        40                  45                  50 gaa gag gct ccc agc ctg agg cct gcc cca ccg ccc atc agt gga ggt      246
Glu Glu Ala Pro Ser Leu Arg Pro Ala Pro Pro Pro Ile Ser Gly Gly
    55                  60                  65 ggc tat cgg gct cgt cca gcc aaa gca gct gcc act caa aag aaa gta      294
Gly Tyr Arg Ala Arg Pro Ala Lys Ala Ala Ala Thr Gln Lys Lys Val
70                  75                  80                  85 gaa aga aaa gcc cct gat gct gga ggc tgt ctt cac gct gac cca gac      342
Glu Arg Lys Ala Pro Asp Ala Gly Gly Cys Leu His Ala Asp Pro Asp
                90                  95                  100 ctg ggg gtg ttg tgt cct aca gga tgt cag ttg caa gag gct ttg cta      390
Leu Gly Val Leu Cys Pro Thr Gly Cys Gln Leu Gln Glu Ala Leu Leu
            105                 110                 115 caa cag gaa agg cca atc aga aat agt gtt gat gag tta aat aac aat      438
Gln Gln Glu Arg Pro Ile Arg Asn Ser Val Asp Glu Leu Asn Asn Asn
        120                 125                 130 gtg gaa gct gtt tcc cag acc tcc tct tct tcc ttt cag tac atg tat      486
Val Glu Ala Val Ser Gln Thr Ser Ser Ser Ser Phe Gln Tyr Met Tyr
    135                 140                 145 ttg ctg aaa gac ctg tgg caa aag agg cag aag caa gta aaa gat aat      534
```

```
                                                                     -continued Leu Leu Lys Asp Leu Trp Gln Lys Arg Gln Lys Gln Val Lys Asp Asn
150                 155                 160                 165 gaa aat gta gtc aat gag tac tcc tca gaa ctg gaa aag cac caa tta      582
Glu Asn Val Val Asn Glu Tyr Ser Ser Glu Leu Glu Lys His Gln Leu
                170                 175                 180 tat ata gat gag act gtg aat agc aat atc cca act aac ctt cgt gtg     630
Tyr Ile Asp Glu Thr Val Asn Ser Asn Ile Pro Thr Asn Leu Arg Val
            185                 190                 195 ctt cgt tca atc ctg gaa aac ctg aga agc aaa ata caa aag tta gaa     678
Leu Arg Ser Ile Leu Glu Asn Leu Arg Ser Lys Ile Gln Lys Leu Glu
        200                 205                 210 tct gat gtc tca gct caa atg gaa tat tgt cgc acc cca tgc act gtc     726
Ser Asp Val Ser Ala Gln Met Glu Tyr Cys Arg Thr Pro Cys Thr Val
    215                 220                 225 agt tgc aat att cct gtg gtg tct ggc aaa gaa tgt gag gaa att atc     774
Ser Cys Asn Ile Pro Val Val Ser Gly Lys Glu Cys Glu Glu Ile Ile
230                 235                 240                 245 agg aaa gga ggt gaa aca tct gaa atg tat ctc att caa cct gac agt     822
Arg Lys Gly Gly Glu Thr Ser Glu Met Tyr Leu Ile Gln Pro Asp Ser
                250                 255                 260 tct gtc aaa ccg tat aga gta tac tgt gac atg aat aca gaa aat gga     870
Ser Val Lys Pro Tyr Arg Val Tyr Cys Asp Met Asn Thr Glu Asn Gly
            265                 270                 275 gga tgg aca gtg att cag aac cgt caa gac ggt agt gtt gac ttt ggc     918
Gly Trp Thr Val Ile Gln Asn Arg Gln Asp Gly Ser Val Asp Phe Gly
        280                 285                 290 agg aaa tgg gat cca tat aaa cag gga ttt gga aat gtt gca acc aac     966
Arg Lys Trp Asp Pro Tyr Lys Gln Gly Phe Gly Asn Val Ala Thr Asn
    295                 300                 305 aca gat ggg aag aat tac tgt ggc cta cca ggt gaa tat tgg ctt gga    1014
Thr Asp Gly Lys Asn Tyr Cys Gly Leu Pro Gly Glu Tyr Trp Leu Gly
310                 315                 320                 325 aat gat aaa att agc cag ctt acc agg atg gga ccc aca gaa ctt ttg    1062
Asn Asp Lys Ile Ser Gln Leu Thr Arg Met Gly Pro Thr Glu Leu Leu
                330                 335                 340 ata gaa atg gag gac tgg aaa gga gac aaa gta aag gct cac tat gga    1110
Ile Glu Met Glu Asp Trp Lys Gly Asp Lys Val Lys Ala His Tyr Gly
            345                 350                 355 gga ttc act gta cag aat gaa gcc aac aaa tac cag atc tca gtg aac    1158
Gly Phe Thr Val Gln Asn Glu Ala Asn Lys Tyr Gln Ile Ser Val Asn
        360                 365                 370 aaa tac aga gga aca gcc ggt aat gcc ctc atg gat gga gca tct cag    1206
Lys Tyr Arg Gly Thr Ala Gly Asn Ala Leu Met Asp Gly Ala Ser Gln
    375                 380                 385 ctg atg gga gaa aac agg acc atg acc att cac aac ggc atg ttc ttc    1254
Leu Met Gly Glu Asn Arg Thr Met Thr Ile His Asn Gly Met Phe Phe
390                 395                 400                 405 agc acg tat gac aga gac aat gac ggc tgg tta aca tca gat ccc aga    1302
Ser Thr Tyr Asp Arg Asp Asn Asp Gly Trp Leu Thr Ser Asp Pro Arg
                410                 415                 420 aaa cag tgt tct aaa gaa gac ggt ggt gga tgg tgg tat aat aga tgt    1350
Lys Gln Cys Ser Lys Glu Asp Gly Gly Gly Trp Trp Tyr Asn Arg Cys
            425                 430                 435 cat gca gcc aat cca aac ggc aga tac tac tgg ggt gga cag tac acc    1398
His Ala Ala Asn Pro Asn Gly Arg Tyr Tyr Trp Gly Gly Gln Tyr Thr
        440                 445                 450 tgg gac atg gca aag cat ggc aca gat gat ggt gta gta tgg atg aat    1446
Trp Asp Met Ala Lys His Gly Thr Asp Asp Gly Val Val Trp Met Asn
    455                 460                 465
```

-continued

| | |
|---|---|
| tgg aag ggg tca tgg tac tca atg agg aag atg agt atg aag atc agg<br>Trp Lys Gly Ser Trp Tyr Ser Met Arg Lys Met Ser Met Lys Ile Arg<br>470                      475                      480                      485 | 1494 |
| ccc ttc ttc cca cag caa tag tccccaatac gtagattttt gctcttctgt<br>Pro Phe Phe Pro Gln Gln<br>                        490 | 1545 |
| atgtgacaac attttgtac attatgttat tggaattttc tttcatacat tatattcctc | 1605 |
| taaaactctc aagcagacgt gagtgtgact ttttgaaaaa agtataggat aaattacatt | 1665 |
| aaaatagcac atgattttct tttgttttct tcatttctct tgctcaccaa gaagtaacaa | 1725 |
| aagtatagtt ttgacagagt tggtgttcat aatttcagtt ctagttgatt gcgagaattt | 1785 |
| tcaaataagg aagagggggtc ttttatcctt gtcgtaggaa aaccatgacg gaaaggaaaa | 1845 |
| actgatgttt aaaagtccac ttttaaaact atatttattt atgtaggatc tgtcaaagaa | 1905 |
| aacttccaaa aagatttatt aattaaacca gactctgttg caataagtta atgttttctt | 1965 |
| gttttgtaat ccacacattc aatgagttag ctttgcact tgtaaggaag agaagcgtt | 2025 |
| cacaacctca aatagctaat aaaccggtct tgaatatttg aagatttaaa atctgactct | 2085 |
| aggacgggca cggtggctca cgactataat cccaacactt tgggaggctg aggcgggcgg | 2145 |
| tcacaaggtc aggagttcaa gaccagcctg accaatatgt gaaaccccca tctctactaa | 2205 |
| aaatacaaaa attagccagg cgtggtggca ggtgcctgta gtcccagcta cctgtgaggt | 2265 |
| ggagattgca ttgagccaag atctcaacac tgcactccag cctgggcaac agcgtgagac | 2325 |
| tccacctcaa aaaaaaaaaa aaagaatct gactatatac catggaaaag ccaccactct | 2385 |
| gccacttaaa taaacatcag gatcagagat tccaagagga caatctgcat caagtcttca | 2445 |
| ccaagtgttt tttaagcgaa ataatgaaat agggagcaga atatgcctgt tgcccataga | 2505 |
| aacgaggtct attcttgtcc tcaattaggc ttttttttct tcatagttac accagaacta | 2565 |
| aagtaaaagt ggttttttctg ttctttctac ttctccccat gaaatgggca tatcatctca | 2625 |
| acacttcact ccaagtcgcc acgggcaacc ttatgaccct aggtcctcca ccctaatgt | 2685 |
| atcatcattg ccacccattt ttatggtact tattgttctt aagcttatcc tcttaatctt | 2745 |
| ttcatgtaag caaagctcat taatttctgt cttggaaatg ctactactct ctttaattac | 2805 |
| tcaccaaatc caactttaac ttttgacctg gtttctctgc cacaagttct gtcccactgg | 2865 |
| agcccatact cacctaccgc tttgccatca catttaacag aaaactctta tcaacttact | 2925 |
| tcctgcttaa cattagctcc ttcctatcta tatccaaatt tcttaaattc aaatttttta | 2985 |
| gctggagtaa aaatggtccc agtaccattt cctgttccct tcactataac ctacattttt | 3045 |
| gtcacattaa gtttttcccc attccaggac aggtcaggcc ctttaaaaat ttcaacagct | 3105 |
| ttattgagat ataattgata taatttaaaa aatcctgcac atgtgtcatg ctggagccct | 3165 |
| attgattcca acagggatgg cgccttgtcc aagaagagac ccagagccag tgaatgggac | 3225 |
| ataggggttta tttaggactt aaatacagat gtggtccagt ggcagtgggc tggacaggac | 3285 |
| cgctactatt tgtaaagagt atgtagttta tataacattt ctactagca ctctccactt | 3345 |
| agcaacctcc atttaacccca aaataaaagg ccttggttcc ttgcacatcc tgagttccaa | 3405 |
| cggacaggca gggagttcaa gtgtccttca cagataagaa gtgaatctct ctgggttggc | 3465 |
| cattcccgga ttccttagct tagactctga acacatattc ttcttagacc atacagtcat | 3525 |
| tctcagggta tgcttgagtt aatgctgtcg gatgcatctg tcatacaaag tgtttaacat | 3585 |
| atacgatttc atgattttgg aaatatgcat acacccatga tat | 3628 |

```
<210> SEQ ID NO 6
<211> LENGTH: 491
<212> TYPE: PRT
<213> ORGANISM: Homo sapiens

<400> SEQUENCE: 6

Met Lys Arg Met Val Ser Trp Ser Phe His Lys Leu Lys Thr Met Lys
1               5                   10                  15

His Leu Leu Leu Leu Leu Cys Val Phe Leu Val Lys Ser Gln Gly
            20                  25                  30

Val Asn Asp Asn Glu Glu Gly Phe Phe Ser Ala Arg Gly His Arg Pro
            35                  40                  45

Leu Asp Lys Lys Arg Glu Glu Ala Pro Ser Leu Arg Pro Ala Pro Pro
        50                  55                  60

Pro Ile Ser Gly Gly Gly Tyr Arg Ala Arg Pro Ala Lys Ala Ala Ala
65                  70                  75                  80

Thr Gln Lys Lys Val Glu Arg Lys Ala Pro Asp Ala Gly Gly Cys Leu
                85                  90                  95

His Ala Asp Pro Asp Leu Gly Val Leu Cys Pro Thr Gly Cys Gln Leu
            100                 105                 110

Gln Glu Ala Leu Leu Gln Gln Glu Arg Pro Ile Arg Asn Ser Val Asp
        115                 120                 125

Glu Leu Asn Asn Asn Val Glu Ala Val Ser Gln Thr Ser Ser Ser Ser
130                 135                 140

Phe Gln Tyr Met Tyr Leu Leu Lys Asp Leu Trp Gln Lys Arg Gln Lys
145                 150                 155                 160

Gln Val Lys Asp Asn Glu Asn Val Val Asn Glu Tyr Ser Ser Glu Leu
                165                 170                 175

Glu Lys His Gln Leu Tyr Ile Asp Glu Thr Val Asn Ser Asn Ile Pro
            180                 185                 190

Thr Asn Leu Arg Val Leu Arg Ser Ile Leu Glu Asn Leu Arg Ser Lys
        195                 200                 205

Ile Gln Lys Leu Glu Ser Asp Val Ser Ala Gln Met Glu Tyr Cys Arg
210                 215                 220

Thr Pro Cys Thr Val Ser Cys Asn Ile Pro Val Val Ser Gly Lys Glu
225                 230                 235                 240

Cys Glu Glu Ile Ile Arg Lys Gly Gly Glu Thr Ser Glu Met Tyr Leu
                245                 250                 255

Ile Gln Pro Asp Ser Ser Val Lys Pro Tyr Arg Val Tyr Cys Asp Met
            260                 265                 270

Asn Thr Glu Asn Gly Gly Trp Thr Val Ile Gln Asn Arg Gln Asp Gly
        275                 280                 285

Ser Val Asp Phe Gly Arg Lys Trp Asp Pro Tyr Lys Gln Gly Phe Gly
290                 295                 300

Asn Val Ala Thr Asn Thr Asp Gly Lys Asn Tyr Cys Gly Leu Pro Gly
305                 310                 315                 320

Glu Tyr Trp Leu Gly Asn Asp Lys Ile Ser Gln Leu Thr Arg Met Gly
                325                 330                 335

Pro Thr Glu Leu Leu Ile Glu Met Glu Asp Trp Lys Gly Asp Lys Val
            340                 345                 350

Lys Ala His Tyr Gly Gly Phe Thr Val Gln Asn Glu Ala Asn Lys Tyr
        355                 360                 365

Gln Ile Ser Val Asn Lys Tyr Arg Gly Thr Ala Gly Asn Ala Leu Met
370                 375                 380
```

```
Asp Gly Ala Ser Gln Leu Met Gly Glu Asn Arg Thr Met Thr Ile His
385                 390                 395                 400

Asn Gly Met Phe Phe Ser Thr Tyr Asp Arg Asp Asn Asp Gly Trp Leu
            405                 410                 415

Thr Ser Asp Pro Arg Lys Gln Cys Ser Lys Glu Asp Gly Gly Gly Trp
        420                 425                 430

Trp Tyr Asn Arg Cys His Ala Ala Asn Pro Asn Gly Arg Tyr Tyr Trp
    435                 440                 445

Gly Gly Gln Tyr Thr Trp Asp Met Ala Lys His Gly Thr Asp Asp Gly
    450                 455                 460

Val Val Trp Met Asn Trp Lys Gly Ser Trp Tyr Ser Met Arg Lys Met
465                 470                 475                 480

Ser Met Lys Ile Arg Pro Phe Phe Pro Gln Gln
                485                 490

<210> SEQ ID NO 7
<211> LENGTH: 1503
<212> TYPE: DNA
<213> ORGANISM: Artificial
<220> FEATURE:
<223> OTHER INFORMATION: human fibrinogen B beta insert cDNA
<220> FEATURE:
<221> NAME/KEY: CDS
<222> LOCATION: (61)..(1497)
<223> OTHER INFORMATION:

<400> SEQUENCE: 7
cacccccggg aagtatttta ctgttttcgt aacagttttg taataaaaaa acctataaat      60 atg ctg cta tcc gtg ccg ttg ctc ctc ggc ctc ctc ggc ctg gcc gtc     108
Met Leu Leu Ser Val Pro Leu Leu Leu Gly Leu Leu Gly Leu Ala Val
1               5                   10                  15 gcc caa ggt gtc aac gac aat gag gag ggt ttc ttc agt gcc cgt ggt     156
Ala Gln Gly Val Asn Asp Asn Glu Glu Gly Phe Phe Ser Ala Arg Gly
            20                  25                  30 cat cga ccc ctt gac aag aag aga gaa gag gct ccc agc ctg agg cct     204
His Arg Pro Leu Asp Lys Lys Arg Glu Glu Ala Pro Ser Leu Arg Pro
        35                  40                  45 gcc cca ccg ccc atc agt gga ggt ggc tat cgg gct cgt cca gcc aaa     252
Ala Pro Pro Pro Ile Ser Gly Gly Gly Tyr Arg Ala Arg Pro Ala Lys
    50                  55                  60 gca gct gcc act caa aag aaa gta gaa aga aaa gcc cct gat gct gga     300
Ala Ala Ala Thr Gln Lys Lys Val Glu Arg Lys Ala Pro Asp Ala Gly
65                  70                  75                  80 ggc tgt ctt cac gct gac cca gac ctg ggg gtg ttg tgt cct aca gga     348
Gly Cys Leu His Ala Asp Pro Asp Leu Gly Val Leu Cys Pro Thr Gly
                85                  90                  95 tgt cag ttg caa gag gct ttg cta caa cag gaa agg cca atc aga aat     396
Cys Gln Leu Gln Glu Ala Leu Leu Gln Gln Glu Arg Pro Ile Arg Asn
            100                 105                 110 agt gtt gat gag tta aat aac aat gtg gaa gct gtt tcc cag acc tcc     444
Ser Val Asp Glu Leu Asn Asn Asn Val Glu Ala Val Ser Gln Thr Ser
        115                 120                 125 tct tct tcc ttt cag tac atg tat ttg ctg aaa gac ctg tgg caa aag     492
Ser Ser Ser Phe Gln Tyr Met Tyr Leu Leu Lys Asp Leu Trp Gln Lys
    130                 135                 140 agg cag aag caa gta aaa gat aat gaa aat gta gtc aat gag tac tcc     540
Arg Gln Lys Gln Val Lys Asp Asn Glu Asn Val Val Asn Glu Tyr Ser
145                 150                 155                 160 tca gaa ctg gaa aag cac caa tta tat ata gat gag act gtg aat agc     588
Ser Glu Leu Glu Lys His Gln Leu Tyr Ile Asp Glu Thr Val Asn Ser
```

```
                        165                 170                 175
aat atc cca act aac ctt cgt gtg ctt cgt tca atc ctg gaa aac ctg        636
Asn Ile Pro Thr Asn Leu Arg Val Leu Arg Ser Ile Leu Glu Asn Leu
        180                 185                 190 aga agc aaa ata caa aag tta gaa tct gat gtc tca gct caa atg gaa        684
Arg Ser Lys Ile Gln Lys Leu Glu Ser Asp Val Ser Ala Gln Met Glu
        195                 200                 205 tat tgt cgc acc cca tgc act gtc agt tgc aat att cct gtg gtg tct        732
Tyr Cys Arg Thr Pro Cys Thr Val Ser Cys Asn Ile Pro Val Val Ser
210                 215                 220 ggc aaa gaa tgt gag gaa att atc agg aaa gga ggt gaa aca tct gaa        780
Gly Lys Glu Cys Glu Glu Ile Ile Arg Lys Gly Gly Glu Thr Ser Glu
225                 230                 235                 240 atg tat ctc att caa cct gac agt tct gtc aaa ccg tat aga gta tac        828
Met Tyr Leu Ile Gln Pro Asp Ser Ser Val Lys Pro Tyr Arg Val Tyr
            245                 250                 255 tgt gac atg aat aca gaa aat gga gga tgg aca gtg att cag aac cgt        876
Cys Asp Met Asn Thr Glu Asn Gly Gly Trp Thr Val Ile Gln Asn Arg
                260                 265                 270 caa gac ggt agt gtt gac ttt ggc agg aaa tgg gat cca tat aaa cag        924
Gln Asp Gly Ser Val Asp Phe Gly Arg Lys Trp Asp Pro Tyr Lys Gln
                    275                 280                 285 gga ttt gga aat gtt gca acc aac aca gat ggg aag aat tac tgt ggc        972
Gly Phe Gly Asn Val Ala Thr Asn Thr Asp Gly Lys Asn Tyr Cys Gly
290                 295                 300 cta cca ggt gaa tat tgg ctt gga aat gat aaa att agc cag ctt acc       1020
Leu Pro Gly Glu Tyr Trp Leu Gly Asn Asp Lys Ile Ser Gln Leu Thr
305                 310                 315                 320 agg atg gga ccc aca gaa ctt ttg ata gaa atg gag gac tgg aaa gga       1068
Arg Met Gly Pro Thr Glu Leu Leu Ile Glu Met Glu Asp Trp Lys Gly
            325                 330                 335 gac aaa gta aag gct cac tat gga gga ttc act gta cag aat gaa gcc       1116
Asp Lys Val Lys Ala His Tyr Gly Gly Phe Thr Val Gln Asn Glu Ala
                340                 345                 350 aac aaa tac cag atc tca gtg aac aaa tac aga gga aca gcc ggt aat       1164
Asn Lys Tyr Gln Ile Ser Val Asn Lys Tyr Arg Gly Thr Ala Gly Asn
                    355                 360                 365 gcc ctc atg gat gga gca tct cag ctg atg gga gaa aac agg acc atg       1212
Ala Leu Met Asp Gly Ala Ser Gln Leu Met Gly Glu Asn Arg Thr Met
370                 375                 380 acc att cac aac ggc atg ttc ttc agc acg tat gac aga gac aat gac       1260
Thr Ile His Asn Gly Met Phe Phe Ser Thr Tyr Asp Arg Asp Asn Asp
385                 390                 395                 400 ggc tgg tta aca tca gat ccc aga aaa cag tgt tct aaa gaa gac ggt       1308
Gly Trp Leu Thr Ser Asp Pro Arg Lys Gln Cys Ser Lys Glu Asp Gly
            405                 410                 415 ggt gga tgg tgg tat aat aga tgt cat gca gcc aat cca aac ggc aga       1356
Gly Gly Trp Trp Tyr Asn Arg Cys His Ala Ala Asn Pro Asn Gly Arg
                420                 425                 430 tac tac tgg ggt gga cag tac acc tgg gac atg gca aag cat ggc aca       1404
Tyr Tyr Trp Gly Gly Gln Tyr Thr Trp Asp Met Ala Lys His Gly Thr
                    435                 440                 445 gat gat ggt gta gta tgg atg aat tgg aag ggg tca tgg tac tca atg       1452
Asp Asp Gly Val Val Trp Met Asn Trp Lys Gly Ser Trp Tyr Ser Met
450                 455                 460 agg aag atg agt atg aag atc agg ccc ttc ttc cca cag caa taa           1497
Arg Lys Met Ser Met Lys Ile Arg Pro Phe Phe Pro Gln Gln
465                 470                 475 cccggg                                                                1503
```

<210> SEQ ID NO 8
<211> LENGTH: 478
<212> TYPE: PRT
<213> ORGANISM: Artificial
<220> FEATURE:
<223> OTHER INFORMATION: human fibrinogen B beta insert cDNA

<400> SEQUENCE: 8

```
Met Leu Leu Ser Val Pro Leu Leu Leu Gly Leu Leu Gly Leu Ala Val
1               5                   10                  15

Ala Gln Gly Val Asn Asp Asn Glu Glu Gly Phe Phe Ser Ala Arg Gly
            20                  25                  30

His Arg Pro Leu Asp Lys Lys Arg Glu Glu Ala Pro Ser Leu Arg Pro
        35                  40                  45

Ala Pro Pro Pro Ile Ser Gly Gly Gly Tyr Arg Ala Arg Pro Ala Lys
    50                  55                  60

Ala Ala Ala Thr Gln Lys Lys Val Glu Arg Lys Ala Pro Asp Ala Gly
65                  70                  75                  80

Gly Cys Leu His Ala Asp Pro Asp Leu Gly Val Leu Cys Pro Thr Gly
                85                  90                  95

Cys Gln Leu Gln Glu Ala Leu Leu Gln Gln Glu Arg Pro Ile Arg Asn
            100                 105                 110

Ser Val Asp Glu Leu Asn Asn Asn Val Glu Ala Val Ser Gln Thr Ser
        115                 120                 125

Ser Ser Ser Phe Gln Tyr Met Tyr Leu Leu Lys Asp Leu Trp Gln Lys
    130                 135                 140

Arg Gln Lys Gln Val Lys Asp Asn Glu Asn Val Val Asn Glu Tyr Ser
145                 150                 155                 160

Ser Glu Leu Glu Lys His Gln Leu Tyr Ile Asp Glu Thr Val Asn Ser
                165                 170                 175

Asn Ile Pro Thr Asn Leu Arg Val Leu Arg Ser Ile Leu Glu Asn Leu
            180                 185                 190

Arg Ser Lys Ile Gln Lys Leu Glu Ser Asp Val Ser Ala Gln Met Glu
        195                 200                 205

Tyr Cys Arg Thr Pro Cys Thr Val Ser Cys Asn Ile Pro Val Val Ser
    210                 215                 220

Gly Lys Glu Cys Glu Glu Ile Ile Arg Lys Gly Gly Glu Thr Ser Glu
225                 230                 235                 240

Met Tyr Leu Ile Gln Pro Asp Ser Ser Val Lys Pro Tyr Arg Val Tyr
                245                 250                 255

Cys Asp Met Asn Thr Glu Asn Gly Gly Trp Thr Val Ile Gln Asn Arg
            260                 265                 270

Gln Asp Gly Ser Val Asp Phe Gly Arg Lys Trp Asp Pro Tyr Lys Gln
        275                 280                 285

Gly Phe Gly Asn Val Ala Thr Asn Thr Asp Gly Lys Asn Tyr Cys Gly
    290                 295                 300

Leu Pro Gly Glu Tyr Trp Leu Gly Asn Asp Lys Ile Ser Gln Leu Thr
305                 310                 315                 320

Arg Met Gly Pro Thr Glu Leu Leu Ile Glu Met Glu Asp Trp Lys Gly
                325                 330                 335

Asp Lys Val Lys Ala His Tyr Gly Gly Phe Thr Val Gln Asn Glu Ala
            340                 345                 350

Asn Lys Tyr Gln Ile Ser Val Asn Lys Tyr Arg Gly Thr Ala Gly Asn
        355                 360                 365
```

```
Ala Leu Met Asp Gly Ala Ser Gln Leu Met Gly Glu Asn Arg Thr Met
        370                 375                 380

Thr Ile His Asn Gly Met Phe Phe Ser Thr Tyr Asp Arg Asp Asn Asp
385                 390                 395                 400

Gly Trp Leu Thr Ser Asp Pro Arg Lys Gln Cys Ser Lys Glu Asp Gly
                405                 410                 415

Gly Gly Trp Trp Tyr Asn Arg Cys His Ala Ala Asn Pro Asn Gly Arg
                420                 425                 430

Tyr Tyr Trp Gly Gly Gln Tyr Thr Trp Asp Met Ala Lys His Gly Thr
            435                 440                 445

Asp Asp Gly Val Val Trp Met Asn Trp Lys Gly Ser Trp Tyr Ser Met
        450                 455                 460

Arg Lys Met Ser Met Lys Ile Arg Pro Phe Phe Pro Gln Gln
465                 470                 475

<210> SEQ ID NO 9
<211> LENGTH: 1665
<212> TYPE: DNA
<213> ORGANISM: Homo sapiens
<220> FEATURE:
<221> NAME/KEY: CDS
<222> LOCATION: (142)..(1455)
<223> OTHER INFORMATION:

<400> SEQUENCE: 9
cttctggtaa ggaggccccg tgatcagctc cagccatttg cagtcctggc tatcccagga      60
gcttacataa agggacaatt ggagcctgag aggtgacagt gctgacacta caaggctcgg     120
agctccgggc actcagacat c atg agt tgg tcc ttg cac ccc cgg aat tta      171
                        Met Ser Trp Ser Leu His Pro Arg Asn Leu
                          1               5                  10 att ctc tac ttc tat gct ctt tta ttt ctc tct tca aca tgt gta gca      219
Ile Leu Tyr Phe Tyr Ala Leu Leu Phe Leu Ser Ser Thr Cys Val Ala
                15                  20                  25 tat gtt gct acc aga gac aac tgc tgc atc tta gat gaa aga ttc ggt      267
Tyr Val Ala Thr Arg Asp Asn Cys Cys Ile Leu Asp Glu Arg Phe Gly
         30                  35                  40 agt tat tgt cca act acc tgt ggc att gca gat ttc ctg tct act tat      315
Ser Tyr Cys Pro Thr Thr Cys Gly Ile Ala Asp Phe Leu Ser Thr Tyr
     45                  50                  55 caa acc aaa gta gac aag gat cta cag tct ttg gaa gac atc tta cat      363
Gln Thr Lys Val Asp Lys Asp Leu Gln Ser Leu Glu Asp Ile Leu His
 60                  65                  70 caa gtt gaa aac aaa aca tca gaa gtc aaa cag ctg ata aaa gca atc      411
Gln Val Glu Asn Lys Thr Ser Glu Val Lys Gln Leu Ile Lys Ala Ile
 75                  80                  85                  90 caa ctc act tat aat cct gat gaa tca tca aaa cca aat atg ata gac      459
Gln Leu Thr Tyr Asn Pro Asp Glu Ser Ser Lys Pro Asn Met Ile Asp
             95                 100                 105 gct gct act ttg aag tcc agg aaa atg tta gaa gaa att atg aaa tat      507
Ala Ala Thr Leu Lys Ser Arg Lys Met Leu Glu Glu Ile Met Lys Tyr
        110                 115                 120 gaa gca tcg att tta aca cat gac tca agt att cga tat ttg cag gaa      555
Glu Ala Ser Ile Leu Thr His Asp Ser Ser Ile Arg Tyr Leu Gln Glu
    125                 130                 135 ata tat aat tca aat aat caa aag att gtt aac ctg aaa gag aag gta      603
Ile Tyr Asn Ser Asn Asn Gln Lys Ile Val Asn Leu Lys Glu Lys Val
140                 145                 150 gcc cag ctt gaa gca cag tgc cag gaa cct tgc aaa gac acg gtg caa      651
```

```
Ala Gln Leu Glu Ala Gln Cys Gln Glu Pro Cys Lys Asp Thr Val Gln
155                 160                 165                 170 atc cat gat atc act ggg aaa gat tgt caa gac att gcc aat aag gga      699
Ile His Asp Ile Thr Gly Lys Asp Cys Gln Asp Ile Ala Asn Lys Gly
                175                 180                 185 gct aaa cag agc ggg ctt tac ttt att aaa cct ctg aaa gct aac cag      747
Ala Lys Gln Ser Gly Leu Tyr Phe Ile Lys Pro Leu Lys Ala Asn Gln
            190                 195                 200 caa ttc tta gtc tac tgt gaa atc gat ggg tct gga aat gga tgg act      795
Gln Phe Leu Val Tyr Cys Glu Ile Asp Gly Ser Gly Asn Gly Trp Thr
        205                 210                 215 gtg ttt cag aag aga ctt gat ggc agt gta gat ttc aag aaa aac tgg      843
Val Phe Gln Lys Arg Leu Asp Gly Ser Val Asp Phe Lys Lys Asn Trp
    220                 225                 230 att caa tat aaa gaa gga ttt gga cat ctg tct cct act ggc aca aca      891
Ile Gln Tyr Lys Glu Gly Phe Gly His Leu Ser Pro Thr Gly Thr Thr
235                 240                 245                 250 gaa ttt tgg ctg gga aat gag aag att cat ttg ata agc aca cag tct      939
Glu Phe Trp Leu Gly Asn Glu Lys Ile His Leu Ile Ser Thr Gln Ser
                255                 260                 265 gcc atc cca tat gca tta aga gtg gaa ctg gaa gac tgg aat ggc aga      987
Ala Ile Pro Tyr Ala Leu Arg Val Glu Leu Glu Asp Trp Asn Gly Arg
            270                 275                 280 acc agt act gca gac tat gcc atg ttc aag gtg gga cct gaa gct gac     1035
Thr Ser Thr Ala Asp Tyr Ala Met Phe Lys Val Gly Pro Glu Ala Asp
        285                 290                 295 aag tac cgc cta aca tat gcc tac ttc gct ggt ggg gat gct gga gat     1083
Lys Tyr Arg Leu Thr Tyr Ala Tyr Phe Ala Gly Gly Asp Ala Gly Asp
    300                 305                 310 gcc ttt gat ggc ttt gat ttt ggc gat gat cct agt gac aag ttt ttc     1131
Ala Phe Asp Gly Phe Asp Phe Gly Asp Asp Pro Ser Asp Lys Phe Phe
315                 320                 325                 330 aca tcc cat aat ggc atg cag ttc agt acc tgg gac aat gac aat gat     1179
Thr Ser His Asn Gly Met Gln Phe Ser Thr Trp Asp Asn Asp Asn Asp
                335                 340                 345 aag ttt gaa ggc aac tgt gct gaa cag gat gga tct ggt tgg tgg atg     1227
Lys Phe Glu Gly Asn Cys Ala Glu Gln Asp Gly Ser Gly Trp Trp Met
            350                 355                 360 aac aag tgt cac gct ggc cat ctc aat gga gtt tat tac caa ggt ggc     1275
Asn Lys Cys His Ala Gly His Leu Asn Gly Val Tyr Tyr Gln Gly Gly
        365                 370                 375 act tac tca aaa gca tct act cct aat ggt tat gat aat ggc att att     1323
Thr Tyr Ser Lys Ala Ser Thr Pro Asn Gly Tyr Asp Asn Gly Ile Ile
    380                 385                 390 tgg gcc act tgg aaa acc cgg tgg tat tcc atg aag aaa acc act atg     1371
Trp Ala Thr Trp Lys Thr Arg Trp Tyr Ser Met Lys Lys Thr Thr Met
395                 400                 405                 410 aag ata atc cca ttc aac aga ctc aca att gga gaa gga cag caa cac     1419
Lys Ile Ile Pro Phe Asn Arg Leu Thr Ile Gly Glu Gly Gln Gln His
                415                 420                 425 cac ctg ggg gga gcc aaa cag gct gga gac gtt taa aagaccgttt          1465
His Leu Gly Gly Ala Lys Gln Ala Gly Asp Val
            430                 435 caaaagagat ttactttttt aaaggacttt atctgaacag agagatataa tattttcct    1525 attggacaat ggacttgcaa agcttcactt catttttaaga gcaaaagacc ccatgttgaa  1585
aactccataa cagtttttatg ctgatgataa tttatctaca tgcatttcaa taaacctttt  1645
gtttcctaag actagaaaaa                                               1665
```

<210> SEQ ID NO 10
<211> LENGTH: 437
<212> TYPE: PRT
<213> ORGANISM: Homo sapiens

<400> SEQUENCE: 10

Met Ser Trp Ser Leu His Pro Arg Asn Leu Ile Leu Tyr Phe Tyr Ala
1               5                   10                  15

Leu Leu Phe Leu Ser Ser Thr Cys Val Ala Tyr Val Ala Thr Arg Asp
            20                  25                  30

Asn Cys Cys Ile Leu Asp Glu Arg Phe Gly Ser Tyr Cys Pro Thr Thr
        35                  40                  45

Cys Gly Ile Ala Asp Phe Leu Ser Thr Tyr Gln Thr Lys Val Asp Lys
    50                  55                  60

Asp Leu Gln Ser Leu Glu Asp Ile Leu His Gln Val Glu Asn Lys Thr
65                  70                  75                  80

Ser Glu Val Lys Gln Leu Ile Lys Ala Ile Gln Leu Thr Tyr Asn Pro
                85                  90                  95

Asp Glu Ser Ser Lys Pro Asn Met Ile Asp Ala Ala Thr Leu Lys Ser
            100                 105                 110

Arg Lys Met Leu Glu Glu Ile Met Lys Tyr Glu Ala Ser Ile Leu Thr
        115                 120                 125

His Asp Ser Ser Ile Arg Tyr Leu Gln Glu Ile Tyr Asn Ser Asn Asn
    130                 135                 140

Gln Lys Ile Val Asn Leu Lys Glu Lys Val Ala Gln Leu Glu Ala Gln
145                 150                 155                 160

Cys Gln Glu Pro Cys Lys Asp Thr Val Gln Ile His Asp Ile Thr Gly
                165                 170                 175

Lys Asp Cys Gln Asp Ile Ala Asn Lys Gly Ala Lys Gln Ser Gly Leu
            180                 185                 190

Tyr Phe Ile Lys Pro Leu Lys Ala Asn Gln Gln Phe Leu Val Tyr Cys
        195                 200                 205

Glu Ile Asp Gly Ser Gly Asn Gly Trp Thr Val Phe Gln Lys Arg Leu
    210                 215                 220

Asp Gly Ser Val Asp Phe Lys Lys Asn Trp Ile Gln Tyr Lys Glu Gly
225                 230                 235                 240

Phe Gly His Leu Ser Pro Thr Gly Thr Thr Glu Phe Trp Leu Gly Asn
                245                 250                 255

Glu Lys Ile His Leu Ile Ser Thr Gln Ser Ala Ile Pro Tyr Ala Leu
            260                 265                 270

Arg Val Glu Leu Glu Asp Trp Asn Gly Arg Thr Ser Thr Ala Asp Tyr
        275                 280                 285

Ala Met Phe Lys Val Gly Pro Glu Ala Asp Lys Tyr Arg Leu Thr Tyr
    290                 295                 300

Ala Tyr Phe Ala Gly Gly Asp Ala Gly Asp Ala Phe Asp Gly Phe Asp
305                 310                 315                 320

Phe Gly Asp Asp Pro Ser Asp Lys Phe Phe Thr Ser His Asn Gly Met
                325                 330                 335

Gln Phe Ser Thr Trp Asp Asn Asp Asn Asp Lys Phe Glu Gly Asn Cys
            340                 345                 350

Ala Glu Gln Asp Gly Ser Gly Trp Trp Met Asn Lys Cys His Ala Gly
        355                 360                 365

His Leu Asn Gly Val Tyr Tyr Gln Gly Gly Thr Tyr Ser Lys Ala Ser
    370                 375                 380

```
Thr Pro Asn Gly Tyr Asp Asn Gly Ile Ile Trp Ala Thr Trp Lys Thr
385                 390                 395                 400

Arg Trp Tyr Ser Met Lys Lys Thr Met Lys Ile Ile Pro Phe Asn
            405                 410                 415

Arg Leu Thr Ile Gly Glu Gly Gln His His Leu Gly Gly Ala Lys
            420                 425                 430

Gln Ala Gly Asp Val
        435

<210> SEQ ID NO 11
<211> LENGTH: 1353
<212> TYPE: DNA
<213> ORGANISM: Artificial
<220> FEATURE:
<223> OTHER INFORMATION: Human fibrinogen gamma insert cDNA
<220> FEATURE:
<221> NAME/KEY: CDS
<222> LOCATION: (61)..(1347)
<223> OTHER INFORMATION:

<400> SEQUENCE: 11
cacccccggg aagtatttta ctgttttcgt aacagttttg taataaaaaa acctataaat      60 atg ctg cta tcc gtg ccg ttg ctg ctc ggc ctc ctc ggc ctg gcc gtc     108
Met Leu Leu Ser Val Pro Leu Leu Leu Gly Leu Leu Gly Leu Ala Val
1               5                   10                  15 gcc tat gtt gct acc aga gac aac tgc tgc atc tta gat gaa aga ttc     156
Ala Tyr Val Ala Thr Arg Asp Asn Cys Cys Ile Leu Asp Glu Arg Phe
            20                  25                  30 ggt agt tat tgt cca act acc tgt ggc att gca gat ttc ctg tct act     204
Gly Ser Tyr Cys Pro Thr Thr Cys Gly Ile Ala Asp Phe Leu Ser Thr
        35                  40                  45 tat caa acc aaa gta gac aag gat cta cag tct ttg gaa gac atc tta     252
Tyr Gln Thr Lys Val Asp Lys Asp Leu Gln Ser Leu Glu Asp Ile Leu
    50                  55                  60 cat caa gtt gaa aac aaa aca tca gaa gtc aaa cag ctg ata aaa gca     300
His Gln Val Glu Asn Lys Thr Ser Glu Val Lys Gln Leu Ile Lys Ala
65                  70                  75                  80 atc caa ctc act tat aat cct gat gaa tca tca aaa cca aat atg ata     348
Ile Gln Leu Thr Tyr Asn Pro Asp Glu Ser Ser Lys Pro Asn Met Ile
                85                  90                  95 gac gct gct act ttg aag tcc agg aaa atg tta gaa gaa att atg aaa     396
Asp Ala Ala Thr Leu Lys Ser Arg Lys Met Leu Glu Glu Ile Met Lys
            100                 105                 110 tat gaa gca tcg att tta aca cat gac tca agt att cga tat ttg cag     444
Tyr Glu Ala Ser Ile Leu Thr His Asp Ser Ser Ile Arg Tyr Leu Gln
        115                 120                 125 gaa ata tat aat tca aat aat caa aag att gtt aac ctg aaa gag aag     492
Glu Ile Tyr Asn Ser Asn Asn Gln Lys Ile Val Asn Leu Lys Glu Lys
    130                 135                 140 gta gcc cag ctt gaa gca cag tgc cag gaa cct tgc aaa gac acg gtg     540
Val Ala Gln Leu Glu Ala Gln Cys Gln Glu Pro Cys Lys Asp Thr Val
145                 150                 155                 160 caa atc cat gat atc act ggg aaa gat tgt caa gac att gcc aat aag     588
Gln Ile His Asp Ile Thr Gly Lys Asp Cys Gln Asp Ile Ala Asn Lys
                165                 170                 175 gga gct aaa cag agc ggg ctt tac ttt att aaa cct ctg aaa gct aac     636
Gly Ala Lys Gln Ser Gly Leu Tyr Phe Ile Lys Pro Leu Lys Ala Asn
            180                 185                 190 cag caa ttc tta gtc tac tgt gaa atc gat ggg tct gga aat gga tgg     684
Gln Gln Phe Leu Val Tyr Cys Glu Ile Asp Gly Ser Gly Asn Gly Trp
```

|  |  |  |  |  |  |  |  |  |  |  |  |  |  |  |  |
|---|---|---|---|---|---|---|---|---|---|---|---|---|---|---|---|
|  | 195 |  |  |  | 200 |  |  |  |  | 205 |  |  |  |  |  |
| act | gtg | ttt | cag | aag | aga | ctt | gat | ggc | agt | gta | gat | ttc | aag | aaa | aac | 732 |
| Thr | Val | Phe | Gln | Lys | Arg | Leu | Asp | Gly | Ser | Val | Asp | Phe | Lys | Lys | Asn |  |
|  | 210 |  |  |  | 215 |  |  |  |  | 220 |  |  |  |  |  |  |
| tgg | att | caa | tat | aaa | gaa | gga | ttt | gga | cat | ctg | tct | cct | act | ggc | aca | 780 |
| Trp | Ile | Gln | Tyr | Lys | Glu | Gly | Phe | Gly | His | Leu | Ser | Pro | Thr | Gly | Thr |  |
| 225 |  |  |  |  | 230 |  |  |  |  | 235 |  |  |  |  | 240 |  |
| aca | gaa | ttt | tgg | ctg | gga | aat | gag | aag | att | cat | ttg | ata | agc | aca | cag | 828 |
| Thr | Glu | Phe | Trp | Leu | Gly | Asn | Glu | Lys | Ile | His | Leu | Ile | Ser | Thr | Gln |  |
|  |  |  |  | 245 |  |  |  |  | 250 |  |  |  |  | 255 |  |  |
| tct | gcc | atc | cca | tat | gca | tta | aga | gtg | gaa | ctg | gaa | gac | tgg | aat | ggc | 876 |
| Ser | Ala | Ile | Pro | Tyr | Ala | Leu | Arg | Val | Glu | Leu | Glu | Asp | Trp | Asn | Gly |  |
|  |  |  | 260 |  |  |  |  | 265 |  |  |  |  | 270 |  |  |  |
| aga | acc | agt | act | gca | gac | tat | gcc | atg | ttc | aag | gtg | gga | cct | gaa | gct | 924 |
| Arg | Thr | Ser | Thr | Ala | Asp | Tyr | Ala | Met | Phe | Lys | Val | Gly | Pro | Glu | Ala |  |
|  |  | 275 |  |  |  |  | 280 |  |  |  |  | 285 |  |  |  |  |
| gac | aag | tac | cgc | cta | aca | tat | gcc | tac | ttc | gct | ggt | ggg | gat | gct | gga | 972 |
| Asp | Lys | Tyr | Arg | Leu | Thr | Tyr | Ala | Tyr | Phe | Ala | Gly | Gly | Asp | Ala | Gly |  |
|  | 290 |  |  |  | 295 |  |  |  |  | 300 |  |  |  |  |  |  |
| gat | gcc | ttt | gat | ggc | ttt | gat | ttt | ggc | gat | gat | cct | agt | gac | aag | ttt | 1020 |
| Asp | Ala | Phe | Asp | Gly | Phe | Asp | Phe | Gly | Asp | Asp | Pro | Ser | Asp | Lys | Phe |  |
| 305 |  |  |  |  | 310 |  |  |  |  | 315 |  |  |  |  | 320 |  |
| ttc | aca | tcc | cat | aat | ggc | atg | cag | ttc | agt | acc | tgg | gac | aat | gac | aat | 1068 |
| Phe | Thr | Ser | His | Asn | Gly | Met | Gln | Phe | Ser | Thr | Trp | Asp | Asn | Asp | Asn |  |
|  |  |  |  | 325 |  |  |  |  | 330 |  |  |  |  | 335 |  |  |
| gat | aag | ttt | gaa | ggc | aac | tgt | gct | gaa | cag | gat | gga | tct | ggt | tgg | tgg | 1116 |
| Asp | Lys | Phe | Glu | Gly | Asn | Cys | Ala | Glu | Gln | Asp | Gly | Ser | Gly | Trp | Trp |  |
|  |  |  | 340 |  |  |  |  | 345 |  |  |  |  | 350 |  |  |  |
| atg | aac | aag | tgt | cac | gct | ggc | cat | ctc | aat | gga | gtt | tat | tac | caa | ggt | 1164 |
| Met | Asn | Lys | Cys | His | Ala | Gly | His | Leu | Asn | Gly | Val | Tyr | Tyr | Gln | Gly |  |
|  |  | 355 |  |  |  |  | 360 |  |  |  |  | 365 |  |  |  |  |
| ggc | act | tac | tca | aaa | gca | tct | act | cct | aat | ggt | tat | gat | aat | ggc | att | 1212 |
| Gly | Thr | Tyr | Ser | Lys | Ala | Ser | Thr | Pro | Asn | Gly | Tyr | Asp | Asn | Gly | Ile |  |
|  | 370 |  |  |  | 375 |  |  |  |  | 380 |  |  |  |  |  |  |
| att | tgg | gcc | act | tgg | aaa | acc | cgg | tgg | tat | tcc | atg | aag | aaa | acc | act | 1260 |
| Ile | Trp | Ala | Thr | Trp | Lys | Thr | Arg | Trp | Tyr | Ser | Met | Lys | Lys | Thr | Thr |  |
| 385 |  |  |  |  | 390 |  |  |  |  | 395 |  |  |  |  | 400 |  |
| atg | aag | ata | atc | cca | ttc | aac | aga | ctc | aca | att | gga | gaa | gga | cag | caa | 1308 |
| Met | Lys | Ile | Ile | Pro | Phe | Asn | Arg | Leu | Thr | Ile | Gly | Glu | Gly | Gln | Gln |  |
|  |  |  |  | 405 |  |  |  |  | 410 |  |  |  |  | 415 |  |  |
| cac | cac | ctg | ggg | gga | gcc | aaa | cag | gct | gga | gac | gtt | taa | cccggg |  |  | 1353 |
| His | His | Leu | Gly | Gly | Ala | Lys | Gln | Ala | Gly | Asp | Val |  |  |  |  |  |
|  |  |  | 420 |  |  |  |  | 425 |  |  |  |  |  |  |  |  |

<210> SEQ ID NO 12
<211> LENGTH: 428
<212> TYPE: PRT
<213> ORGANISM: Artificial
<220> FEATURE:
<223> OTHER INFORMATION: Human fibrinogen gamma insert cDNA

<400> SEQUENCE: 12

Met Leu Leu Ser Val Pro Leu Leu Leu Gly Leu Leu Gly Leu Ala Val
1               5                   10                  15

Ala Tyr Val Ala Thr Arg Asp Asn Cys Cys Ile Leu Asp Glu Arg Phe
                20                  25                  30

Gly Ser Tyr Cys Pro Thr Thr Cys Gly Ile Ala Asp Phe Leu Ser Thr
            35                  40                  45

Tyr Gln Thr Lys Val Asp Lys Asp Leu Gln Ser Leu Glu Asp Ile Leu
        50                  55                  60

His Gln Val Glu Asn Lys Thr Ser Glu Val Lys Gln Leu Ile Lys Ala
 65                  70                  75                  80

Ile Gln Leu Thr Tyr Asn Pro Asp Glu Ser Lys Pro Asn Met Ile
             85                  90                  95

Asp Ala Ala Thr Leu Lys Ser Arg Lys Met Leu Glu Glu Ile Met Lys
             100                 105                 110

Tyr Glu Ala Ser Ile Leu Thr His Asp Ser Ser Ile Arg Tyr Leu Gln
             115                 120                 125

Glu Ile Tyr Asn Ser Asn Asn Gln Lys Ile Val Asn Leu Lys Glu Lys
130                 135                 140

Val Ala Gln Leu Glu Ala Gln Cys Gln Glu Pro Cys Lys Asp Thr Val
145                 150                 155                 160

Gln Ile His Asp Ile Thr Gly Lys Asp Cys Gln Asp Ile Ala Asn Lys
                 165                 170                 175

Gly Ala Lys Gln Ser Gly Leu Tyr Phe Ile Lys Pro Leu Lys Ala Asn
             180                 185                 190

Gln Gln Phe Leu Val Tyr Cys Glu Ile Asp Gly Ser Gly Asn Gly Trp
             195                 200                 205

Thr Val Phe Gln Lys Arg Leu Asp Gly Ser Val Asp Phe Lys Lys Asn
210                 215                 220

Trp Ile Gln Tyr Lys Glu Gly Phe Gly His Leu Ser Pro Thr Gly Thr
225                 230                 235                 240

Thr Glu Phe Trp Leu Gly Asn Glu Lys Ile His Leu Ile Ser Thr Gln
                 245                 250                 255

Ser Ala Ile Pro Tyr Ala Leu Arg Val Glu Leu Glu Asp Trp Asn Gly
             260                 265                 270

Arg Thr Ser Thr Ala Asp Tyr Ala Met Phe Lys Val Gly Pro Glu Ala
             275                 280                 285

Asp Lys Tyr Arg Leu Thr Tyr Ala Tyr Phe Ala Gly Gly Asp Ala Gly
             290                 295                 300

Asp Ala Phe Asp Gly Phe Asp Phe Gly Asp Asp Pro Ser Asp Lys Phe
305                 310                 315                 320

Phe Thr Ser His Asn Gly Met Gln Phe Ser Thr Trp Asp Asn Asp Asn
                 325                 330                 335

Asp Lys Phe Glu Gly Asn Cys Ala Glu Gln Asp Gly Ser Gly Trp Trp
             340                 345                 350

Met Asn Lys Cys His Ala Gly His Leu Asn Gly Val Tyr Tyr Gln Gly
             355                 360                 365

Gly Thr Tyr Ser Lys Ala Ser Thr Pro Asn Gly Tyr Asp Asn Gly Ile
             370                 375                 380

Ile Trp Ala Thr Trp Lys Thr Arg Trp Tyr Ser Met Lys Lys Thr Thr
385                 390                 395                 400

Met Lys Ile Ile Pro Phe Asn Arg Leu Thr Ile Gly Glu Gly Gln Gln
                 405                 410                 415

His His Leu Gly Gly Ala Lys Gln Ala Gly Asp Val
             420                 425

<210> SEQ ID NO 13
<211> LENGTH: 17
<212> TYPE: DNA
<213> ORGANISM: Artificial
<220> FEATURE:
<223> OTHER INFORMATION: primer alpha Bam1 F1

<400> SEQUENCE: 13

```
ttctttcagc tggagtg                                                    17
```

<210> SEQ ID NO 14
<211> LENGTH: 16
<212> TYPE: DNA
<213> ORGANISM: Artificial
<220> FEATURE:
<223> OTHER INFORMATION: primer alpha Hind3 R1

<400> SEQUENCE: 14

```
aaggaaatgc aagggg                                                     16
```

<210> SEQ ID NO 15
<211> LENGTH: 28
<212> TYPE: DNA
<213> ORGANISM: Artificial
<220> FEATURE:
<223> OTHER INFORMATION: primer alpha Bam1 F2

<400> SEQUENCE: 15

```
gcgggatcca tgttttccat gaggatcg                                        28
```

<210> SEQ ID NO 16
<211> LENGTH: 25
<212> TYPE: DNA
<213> ORGANISM: Artificial
<220> FEATURE:
<223> OTHER INFORMATION: primer alpha Hind3 R2

<400> SEQUENCE: 16

```
gcgaagcttc taggggaca gggaa                                            25
```

<210> SEQ ID NO 17
<211> LENGTH: 51
<212> TYPE: DNA
<213> ORGANISM: Artificial
<220> FEATURE:
<223> OTHER INFORMATION: primer Fibrinogen Alpha N1

<400> SEQUENCE: 17

```
tcggcctcct cggcctggcc gtcgccgcag atagtggtga aggtgacttt c              51
```

<210> SEQ ID NO 18
<211> LENGTH: 27
<212> TYPE: DNA
<213> ORGANISM: Artificial
<220> FEATURE:
<223> OTHER INFORMATION: primer Fibrinogen Alpha C1

<400> SEQUENCE: 18

```
cccgggttag acagggcgag atttagc                                         27
```

<210> SEQ ID NO 19
<211> LENGTH: 45
<212> TYPE: DNA
<213> ORGANISM: Artificial
<220> FEATURE:
<223> OTHER INFORMATION: primer Fibrinogen ATG N2

<400> SEQUENCE: 19

```
atgctgctat ccgtgccgtt gctgctcggc ctcctcggcc tggcc                     45
```

<210> SEQ ID NO 20
<211> LENGTH: 45
<212> TYPE: DNA

```
<213> ORGANISM: Artificial
<220> FEATURE:
<223> OTHER INFORMATION: primer Fibrinogen UTR N3

<400> SEQUENCE: 20
gtaataaaaa aacctataaa tatgctgcta tccgtgccgt tgctg              45

<210> SEQ ID NO 21
<211> LENGTH: 56
<212> TYPE: DNA
<213> ORGANISM: Artificial
<220> FEATURE:
<223> OTHER INFORMATION: primer Fibrinogen UTR N4

<400> SEQUENCE: 21
caccccgggg aagtatttta ctgttttcgt aacagttttg taataaaaaa acctat   56

<210> SEQ ID NO 22
<211> LENGTH: 20
<212> TYPE: DNA
<213> ORGANISM: Artificial
<220> FEATURE:
<223> OTHER INFORMATION: primer beta EcoR1 F1

<400> SEQUENCE: 22
gatctctcag ttaagtctac                                          20

<210> SEQ ID NO 23
<211> LENGTH: 17
<212> TYPE: DNA
<213> ORGANISM: Artificial
<220> FEATURE:
<223> OTHER INFORMATION: primer beta Xho1 R1

<400> SEQUENCE: 23
tcacatacag aagagca                                             17

<210> SEQ ID NO 24
<211> LENGTH: 30
<212> TYPE: DNA
<213> ORGANISM: Artificial
<220> FEATURE:
<223> OTHER INFORMATION: primer beta EcoR1 F2

<400> SEQUENCE: 24
gcggaattca tgaaaaggat ggtttcttgg                               30

<210> SEQ ID NO 25
<211> LENGTH: 24
<212> TYPE: DNA
<213> ORGANISM: Artificial
<220> FEATURE:
<223> OTHER INFORMATION: primer beta Xho1 R2

<400> SEQUENCE: 25
gcgctcgagc tattgctgtg ggaa                                     24

<210> SEQ ID NO 26
<211> LENGTH: 40
<212> TYPE: DNA
<213> ORGANISM: Artificial
<220> FEATURE:
<223> OTHER INFORMATION: primer Beta-ATG N2

<400> SEQUENCE: 26
tcctcggcct ggccgtcgcc caaggtgtca acgacaatga                    40
```

<210> SEQ ID NO 27
<211> LENGTH: 25
<212> TYPE: DNA
<213> ORGANISM: Artificial
<220> FEATURE:
<223> OTHER INFORMATION: primer Beta-C

<400> SEQUENCE: 27
cccgggttat tgctgtggga agaag                                              25

<210> SEQ ID NO 28
<211> LENGTH: 71
<212> TYPE: DNA
<213> ORGANISM: Artificial
<220> FEATURE:
<223> OTHER INFORMATION: primer Beta-ATG N

<400> SEQUENCE: 28
atgctgctat ccgtgccgtt gctgctcggc ctcctcggcc tggccgtcgc ccaaggtgtc        60
aacgacaatg a                                                             71

<210> SEQ ID NO 29
<211> LENGTH: 16
<212> TYPE: DNA
<213> ORGANISM: Artificial
<220> FEATURE:
<223> OTHER INFORMATION: primer gamma EcoR1 F1

<400> SEQUENCE: 29
aattggagcc tgagag                                                        16

<210> SEQ ID NO 30
<211> LENGTH: 16
<212> TYPE: DNA
<213> ORGANISM: Artificial
<220> FEATURE:
<223> OTHER INFORMATION: primer gamma Hind3 R1

<400> SEQUENCE: 30
gtgaagcttt gcaagt                                                        16

<210> SEQ ID NO 31
<211> LENGTH: 28
<212> TYPE: DNA
<213> ORGANISM: Artificial
<220> FEATURE:
<223> OTHER INFORMATION: primer gamma EcoR1 F2

<400> SEQUENCE: 31
gcggaattca tgagttggtc cttgcacc                                           28

<210> SEQ ID NO 32
<211> LENGTH: 26
<212> TYPE: DNA
<213> ORGANISM: Artificial
<220> FEATURE:
<223> OTHER INFORMATION: primer gamma Hind3 R2

<400> SEQUENCE: 32
gcgctcgagt taaacgtctc cagcct                                             26

<210> SEQ ID NO 33
<211> LENGTH: 51
<212> TYPE: DNA

```
<213> ORGANISM: Artificial
<220> FEATURE:
<223> OTHER INFORMATION: primer Fibrinogen gamma N1

<400> SEQUENCE: 33
tcggcctcct cggcctggcc gtcgcctatg ttgctaccag agacaactgc t         51

<210> SEQ ID NO 34
<211> LENGTH: 27
<212> TYPE: DNA
<213> ORGANISM: Artificial
<220> FEATURE:
<223> OTHER INFORMATION: primer Fibrinogen gamma C1

<400> SEQUENCE: 34
cccgggttaa acgtctccag cctgttt                                    27
```

FIBRINOGEN-PRODUCING TRANSGENIC SILKWORM

TECHNICAL FIELD

The present invention relates to a transgenic silkworm that produces fibrinogen having coagulation activity in the cocoon filament, a method for producing the silkworm, and a method for producing fibrinogen.

BACKGROUND ART

Fibrinogen is a plasma protein present in blood plasma, and is a glycoprotein with a molecular weight of 340 kDa. Fibrinogen has a hexameric molecular structure wherein three chains, that is, the Aα chain, Bβ chain and γ chain, are bound to one another via disulfide bonds and the resulting complex forms a dimer $(A\alpha\text{-}B\beta\text{-}\gamma)_2$. The Aα chain, with a size of 67 kDa, is composed of 610 amino acid residues and does not have a sugar chain. The Bβ chain, with a size of 56 kDa, is composed of 461 amino acid residues and has a sugar chain at Asn at position 364. The γ chain, with a size of 48 kDa, is composed of 411 amino acid residues and has a sugar chain at Asn at position 52.

Fibrinogen is involved in blood coagulation. In the living body, thrombin cleaves the Aα and Bβ chains of fibrinogen to remove the fibrinopeptide A and the fibrinopeptide B, thereby converting fibrinogen into $(\alpha\text{-}\beta\text{-}\gamma)_2$ (fibrinomonomer). The fibrinomonomer is polymerized in the presence of $Ca^{2+}$ to form a fibrin polymer. Further, upon activation of blood coagulation factor XIII by thrombin, the transglutaminase activity of the factor causes formation of peptide bonds among fibrin polymers, to form strongly cross-linked fibrin.

The fibrinogen currently used in the medical field is manufactured by separation and purification from human blood plasma. Since human blood plasma is used as a raw material, there is the risk of contamination with viruses, so that a process such as inactivation of sources of infection is indispensable. Furthermore, since supply of human plasma as a raw material is dependent on blood donation, its constant and stable supply is not always easy.

By production of fibrinogen using gene recombination technology, safe fibrinogen can be stably provided. Such attempts have been reported several times so far, but none of them succeeded in providing a sufficiently efficient and satisfactory method. For example, in Patent Document 1 and Non-patent Document 1, a method for producing a recombinant fibrinogen using a *Pichia* yeast has been disclosed, but, in this method, fibrinogen secreted into the culture liquid is degraded by protease, so that the production method is not efficient. Patent Documents 2 and 3 disclose a method for producing a recombinant fibrinogen using animal cultured cells. However, the production is too costly and laborious to realize commercial production of fibrinogen since, for example, large-scale facilities for cell culture and control of the culture density are required. Further, since animal cells are used, there is the risk of contamination with animal-derived substances and infectious viruses, so that the method has the same problem as the current method wherein fibrinogen is manufactured from human blood.

PRIOR ART DOCUMENTS

Patent Documents

Patent Document 1: JP 2004-16055 A
Patent Document 2: JP 4573775 B
Patent Document 3: JP 2009-528843 A Non-Patent Documents Non-patent Document 1: Protein Expression and Purification 59 (2008) 289-296

SUMMARY OF THE INVENTION

Problems to be Solved by the Invention

Accordingly, the present invention aims to provide a novel means that enables mass production of highly safe fibrinogen at low cost.

Means for Solving the Problems

The present inventors arrived at the idea of producing fibrinogen by a known recombinant protein production technique using a silkworm, and attempted to express the genes for the Aα chain, Bβ chain and γ chain of fibrinogen in the silk glands of a silkworm and then to recover fibrinogen from the cocoon. They tried to prepare a silkworm expressing the Bβ chain and a silkworm expressing the Aα chain and the γ chain and then to cross them to obtain a silkworm expressing the three chains, but no secretion of the Bβ chain into the cocoon could be found in the Bβ chain-expressing silkworm. However, when this Bβ chain-expressing silkworm was crossed with the Aα chain/γ chain-expressing silkworm, fibrinogen having coagulation activity was successfully secreted into the cocoon filament. Further, the present inventors found conditions where fibrinogen can be efficiently recovered from the cocoon filament, thereby completing the present invention.

That is, the present invention provides a transgenic silkworm which expresses fibrinogen subunit Aα, Bβ and γ chains in silk gland cells and produces fibrinogen having coagulation activity in the cocoon filament. The present invention also provides a silkworm cocoon produced by the transgenic silkworm according to the present invention, said silkworm cocoon comprising fibrinogen having coagulation activity. The present invention further provides a method for producing fibrinogen, said method comprising recovering fibrinogen from the cocoon of the transgenic silkworm according to the present invention. The present invention further provides a method for preparing a transgenic silkworm that produces fibrinogen having coagulation activity in the cocoon filament, said method comprising: introducing the fibrinogen subunit Aα, Bβ and γ genes each functionally linked to a promoter that functions in silk gland cells into silkworms; and selecting a silkworm that expresses the Aα, Bβ and γ chains in silk gland cells.

EFFECT OF THE INVENTION

By the present invention, a transgenic silkworm that secretes fibrinogen having coagulation activity into the cocoon filament was provided for the first time. In particular, expression of the Aα, Bβ and γ genes in the middle silk gland is advantageous for recovery of active fibrinogen since fibrinogen is secreted into the sericin layer, which is a relatively water-soluble part in the cocoon filament. Silkworms are organisms having high protein synthetic capacity, and can be easily kept. Unlike production of fibrinogen from a blood material collected by blood donation, the risk of contamination with viruses can be eliminated. By the present invention, highly safe fibrinogen can be mass-produced at low cost.

MODE FOR CARRYING OUT THE INVENTION

Figure 1:
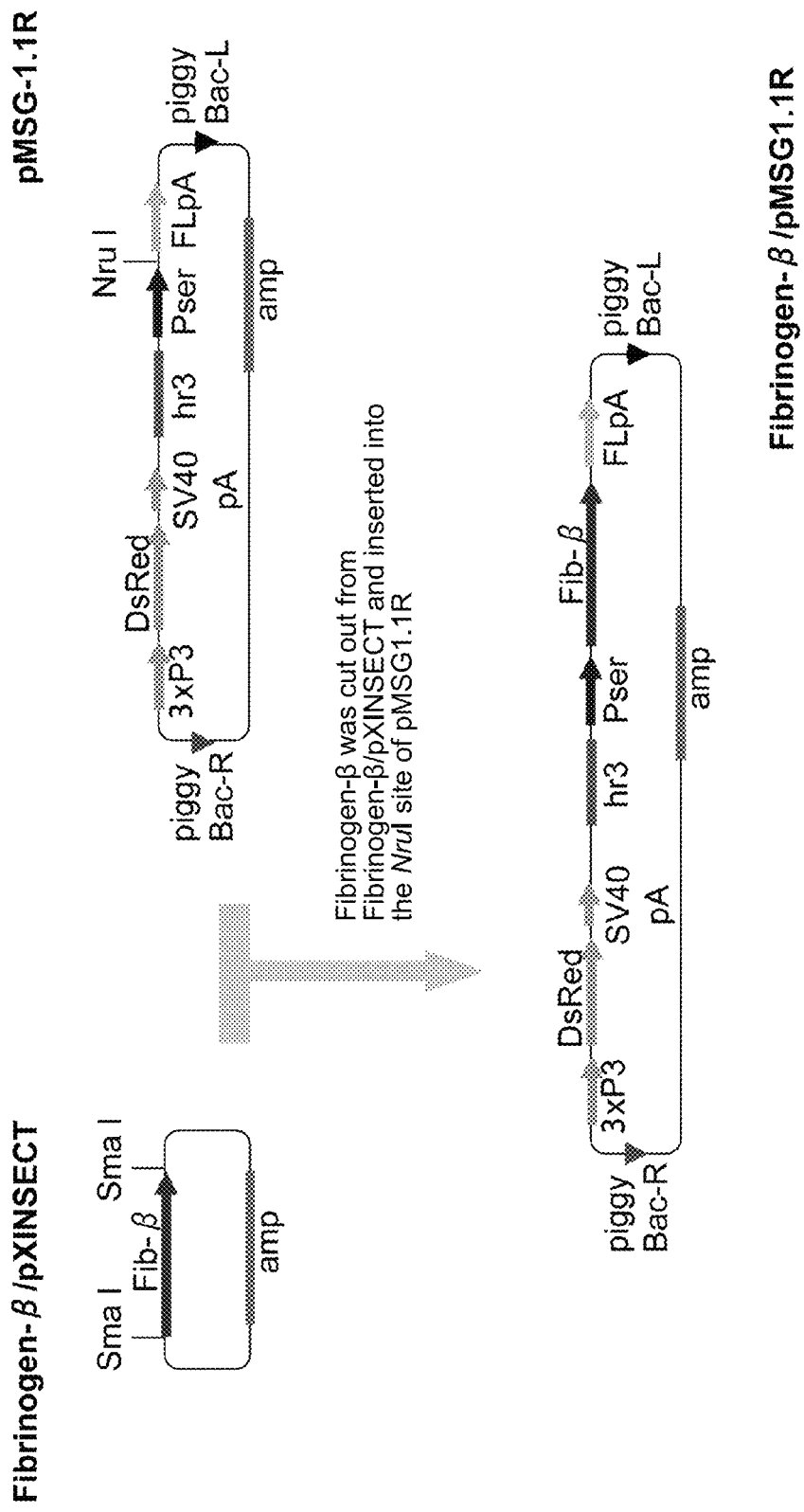
FIG. 1 shows a construction diagram for the vector used for preparation of the Bβ-introduced silkworm in Examples.

The transgenic silkworm of the present invention expresses the three subunits of fibrinogen, the Aα chain, Bβ chain and γ chain, in silk gland cells. A silk gland is an organ that synthesizes and secretes silk threads, and expression of a recombinant protein in silk gland cells causes secretion of the protein together with silk threads, resulting in accumulation of the protein in the cocoon. The silk gland can be divided into three parts, the anterior part, the middle part and the posterior part. Fibroin is secreted from the posterior part, and sericin is secreted from the middle part. The central portion of the silk thread is constituted by figroin, and covered with sericin. Expression of the subunit genes in the posterior silk gland causes secretion of fibrinogen into the fibroin layer of the cocoon filament, and expression of the subunit genes in the middle silk gland causes secretion of fibrinogen into the sericin layer. Since the recombinant protein secreted into the sericin layer can be easily dissolved by immersion of the cocoon filament in water or an aqueous buffer, the protein can be easily recovered from the cocoon while its activity is maintained. Hence, it is preferred that the transgenic silkworm of the present invention express the three subunit genes in the middle silk gland.

Amino acid sequences of human fibrinogen and base sequences encoding them are known, and registered in GenBank under the accession numbers of, for example, NM_021871 (Aα chain), NM_005141 (Bβ chain) and NM_000509 (γ chain). These known sequences are shown in SEQ ID NOs:1 and 2 (cDNA sequence and amino acid sequence of the Aα chain), SEQ ID NOs:5 and 6 (cDNA sequence and amino acid sequence of the Bβ chain) and SEQ ID NOs:9 and 10 (cDNA sequence and amino acid sequence of the γ chain), respectively. The Aα, Bβ, and γ genes to be incorporated into a vector(s) for transformation of a silkworm can be easily obtained by appropriately designing primers based on known sequence information also described in SEQUENCE LISTING of the present application and amplifying the genes from a human cDNA library by conventional PCR.

When the fibrinogen subunit genes are introduced into a silkworm, the original signal peptide region of each subunit is preferably replaced with the signal peptide region of human calreticulin. Since the signal peptide of human calreticulin functions well in silk gland cells of a silkwoiin, it is advantageous for efficient secretion of a recombinant fibrinogen into the cocoon filament. The cDNA sequence and the amino acid sequence of each subunit whose signal peptide was replaced with the signal peptide of human calreticulin are shown in SEQ ID NOs:3 and 4 (Aα chain), SEQ ID NOs:7 and 8 (Bβ chain) and SEQ ID NOs:11 and 12 (γ chain), respectively. The region encoding the signal peptide of human calreticulin corresponds to 64 nt to 111 nt of SEQ ID NO:3. Each of the base sequences shown in SEQ ID NOs:3, 7 and 11 comprises sequences for incorporation into a vector (e.g., a restriction enzyme recognition site) and BmNPV polyhedrin 5'-UTR (11 nt to 60 nt of SEQ ID NO:3) that was added for the purpose of promoting translation. Such modification of a sequence can be easily carried out by PCR using a primer having the desired additional sequence. Its specific procedure is as described in detail in Examples below.

Examples of the procedure for introducing the three subunit genes into a silkworm include a procedure in which the three genes are introduced at the same time, a procedure in which a silkworm into which any one of the three genes has been introduced is crossed with a silkworm into which the other two genes have been introduced at the same time, and a procedure in which silkworms each prepared by introducing a single gene are sequentially crossed. In cases where a plurality of genes are introduced at the same time, the plurality of genes may be incorporated into a single vector, or a plurality of vectors each carrying a single gene may be introduced at the same time to a silkworm. In the Examples below, a vector carrying only the Bβ gene and a vector carrying 2 genes, the Aα gene and the γ gene, were constructed to obtain a Bβ-introduced silkworm and an Aα/γ-introduced silkworm, and these silkworms were crossed to obtain an Aα/Bβ/γ-introduced silkworm. However, the method of introduction of the three genes is not limited thereto.

In order to express the fibrinogen subunits in the silk gland, the Aα, Bβ and γ genes may be introduced into a silkworm in a state where these genes are each functionally linked to a promoter that functions in silk gland cells. The term "functionally linked" herein means that each gene sequence is linked to the downstream region of the promoter such that the gene is under the control of the promoter. The promoter that functions in silk gland cells may be any one as long as it initiates expression of a gene downstream thereof in silk gland cells, and may be a promoter that also functions in other tissues/cells. The promoter that specifically functions in the silk gland cells of interest is preferred. Preferred examples of the promoter that functions in the middle silk gland include those of the sericin genes (e.g., sericin 1 gene and sericin 2 gene), and preferred examples of the promoter that functions in the posterior silk gland include promoters of the fibroin heavy chain gene, fibroin light chain gene and fibrohexamerin gene. However, the promoter is not limited to these. In the present invention, it is preferred that the fibrinogen subunit genes be expressed in the middle silk gland, and therefore a promoter that functions in the middle silk gland, such as the sericin gene promoter, is preferably used.

In view of increasing the expression levels, the three subunit genes are preferably introduced in combination with an enhancer(s). The enhancer, a cis-element of transcription regulation, is provided in the vicinity of a promoter(s) and a subunit gene(s). The enhancer may be located either upstream or downstream of the promoter(s) and the subunit gene(s), and is usually placed upstream of the promoter(s). Further, since a single enhancer can promote transcription of a plurality of genes in its vicinity, a single enhancer may be combined with, for example, two sets of the promoter+subunit gene. For example, in the specific example of the gene transfer vector shown in FIG. 3, one enhancer is inserted for two subunit genes. The enhancer is not limited as long as it is capable of enhancing the transcription activity of a promoter(s) employed, and those skilled in the art can appropriately evaluate the effect of enhancers to enhance the transcription activity using a transient expression system, and select a preferred enhancer. Preferred specific examples of the enhancer which may be used in the present invention include the homologous region of baculoviruses, and hr3 derived from BmNPV may be especially preferably used (see JP 4271122 B). Since sequences of baculovirus-derived enhancers such as hr3 are known (e.g., GenBank NC_001962 and NC_001623) and since the enhancers are also used in commercially available expression vectors for insect cells and the like, the enhancer can be easily obtained by PCR amplification from a baculovirus genome or a commercially available vector as appropriate.

Similarly, in view of increasing the expression levels, the three subunits are preferably introduced in combination with a transactivator(s). A transactivator is a factor that directly or indirectly acts on a promoter to activate transcription of a gene. A transactivator and a subunit gene(s) may be inserted into the same vector and introduced at the same time, or a transactivator may be introduced into a silkworm separately from the subunit genes. For example, the transactivator gene may be inserted into a vector which is different from the vector(s) containing the subunit genes, and the resulting vector may be introduced into a silkworm together with the vector(s) containing the subunit genes. Alternatively, an Aα/Bβ/γ-introduced silkworm may be prepared in advance by introduction of the three subunit genes, and the transactivator gene may be then introduced into this silkworm by a genetic engineering method or by crossing with a transactivator-expressing silkworm which has been separately prepared. The term "introducing a subunit gene(s) in combination with a transactivator(s)" includes all of these modes. The transactivator is not limited as long as it can increase the action of a promoter(s) to be employed (or an enhancer(s) to be employed in cases of a transactivator that acts on an enhancer(s)) on the transcription. Those skilled in the art can appropriately evaluate the activity using a transient expression system to select a preferred transactivator. Preferred specific examples of the transactivator which may be used in the present invention include transcription factor IE1 derived from a baculovirus (see JP 4271122 B). When introducing a transactivator into a silkworm by a genetic engineering method, the same promoter as the one used for the fibrinogen subunit gene(s) may be used. Since sequences of the IE1 gene are also known (e.g., GenBank AY048770 and M16820) and the gene is also used in commercially-available expression vectors for insect cells and the like, the gene can be easily obtained by PCR amplification from a baculovirus genome or a commercially available vector, as appropriate. Further, as was used in the Examples below, IE1-expressing silkworm strains are known (FEBS Journal 276, 5806-5820 (2009), Biotechnol Bioeng 106, 860-870 (2010)).

More preferably, both an enhancer(s) and a transactivator(s) are introduced in combination with the fibrinogen subunit genes. As described in the Examples below, when the IE1 gene is introduced into an Aα/Bβ/γ-introduced silkworm (in which hr3 is used as an enhancer), the weight of the cocoon decreases depending on the expression level of IE1, but the expression levels of the three fibrinogen subunits largely increase and their contents in the cocoon filament also largely increase, and as a consequence, the production efficiency of fibrinogen can be further improved.

In the present invention, the term "introduced in combination" means that an enhancer(s) and/or a transactivator(s) is/are introduced into a silkworm such that the introduced enhancer(s) and/or transactivator(s) contribute(s) to increased expression of the fibrinogen subunit gene(s) in silk gland cells. In cases where an enhancer is introduced in combination with the subunit gene(s), the enhancer is introduced such that it is present in the vicinity of the promoter(s) and the subunit gene(s). Usually, the enhancer is incorporated in the vicinity of a subunit gene(s) in a gene transfer vector, and then introduced into a silkworm together with the subunit gene(s). As described above, unlike the enhancer, the transactivator does not need to be positioned in the vicinity of a subunit gene(s). Therefore, when the term "transactivator is introduced in combination with a subunit gene(s)" is mentioned, it includes the above-described modes, for example, a mode wherein a transactivator is subsequently introduced into a transgenic silkworm that expresses the three subunit genes.

The method per se for introducing a foreign gene into a silkworm is known, and various vectors for transformation of silkworms are also known (e.g., Nature Biotechnology. 21, 52-56, 2003; J Biosci Bioeng 105, 595-603 (2008); FEBS Journal 276, 5806-5820 (2009); JP 2002-306167 A and JP 2008-67612 A). Vectors commonly used for transformation of silkworms at present are vectors using DNA transposons derived from insects, and the most representative example thereof is a plasmid vector using piggyBac. The plasmid vector contains two inverted repeats that are present at both ends of the transposon piggyBac. The sequence to be incorporated into the silkworm chromosome is inserted between the repeats. Microinjection of the resulting vector into a silkworm egg together with a transposase-expressing helper plasmid causes transposition of the region between the repeats by the action of transposase, so that a silkworm comprising the region incorporated into its chromosome can be obtained. Also for preparation of the transgenic silkworm of the present invention, such a piggyBac vector may be preferably used. However, the method to be used is not limited thereto, and any known method may be used.

For convenience in selection, the vector for transformation of a silkworm usually contains a marker gene which is to be incorporated into the silkworm chromosome together with the subunit gene(s). The expression of the transgene(s) can be indirectly confirmed by observing expression of a marker gene in the silkworm individual (egg, larva or adult) into which the vector has been introduced. Thus, a transgenic silkworm may be selected based on the expression of a marker gene. In the method for preparing a transgenic silkworm of the present invention, the step of "selecting a silkworm that expresses the Aα chain, Bβ chain and γ chain in silk gland cells" may be such a step wherein the expression of the subunit genes is indirectly confirmed by the expression of a marker gene(s), thereby carrying out the selection.

The marker is preferably a marker which can be detected, without chemical treatment or mechanical treatment, while the silkworm is kept alive. Preferred examples of the marker that may be used include fluorescent proteins. In cases where, as described in the Examples below, the three subunit genes are divided into two groups to prepare two types of transgenic silkworms and these silkworms are crossed to obtain a silkworm into which the three genes have been introduced, the genes for two kinds of fluorescent proteins whose fluorescence wavelengths are different from each other may be used to prepare the two types of silkworms. For example, in cases where a red fluorescent protein is used as one of the markers and a green fluorescent protein is used as the other marker, yellow fluorescence generated by the combination of red fluorescence and green fluorescence can be observed in the silkworm into which both markers have been introduced by the crossing. Thus, using the yellow fluorescence as an indicator, a silkworm into which the three genes have been introduced can be selected.

Figure 2:
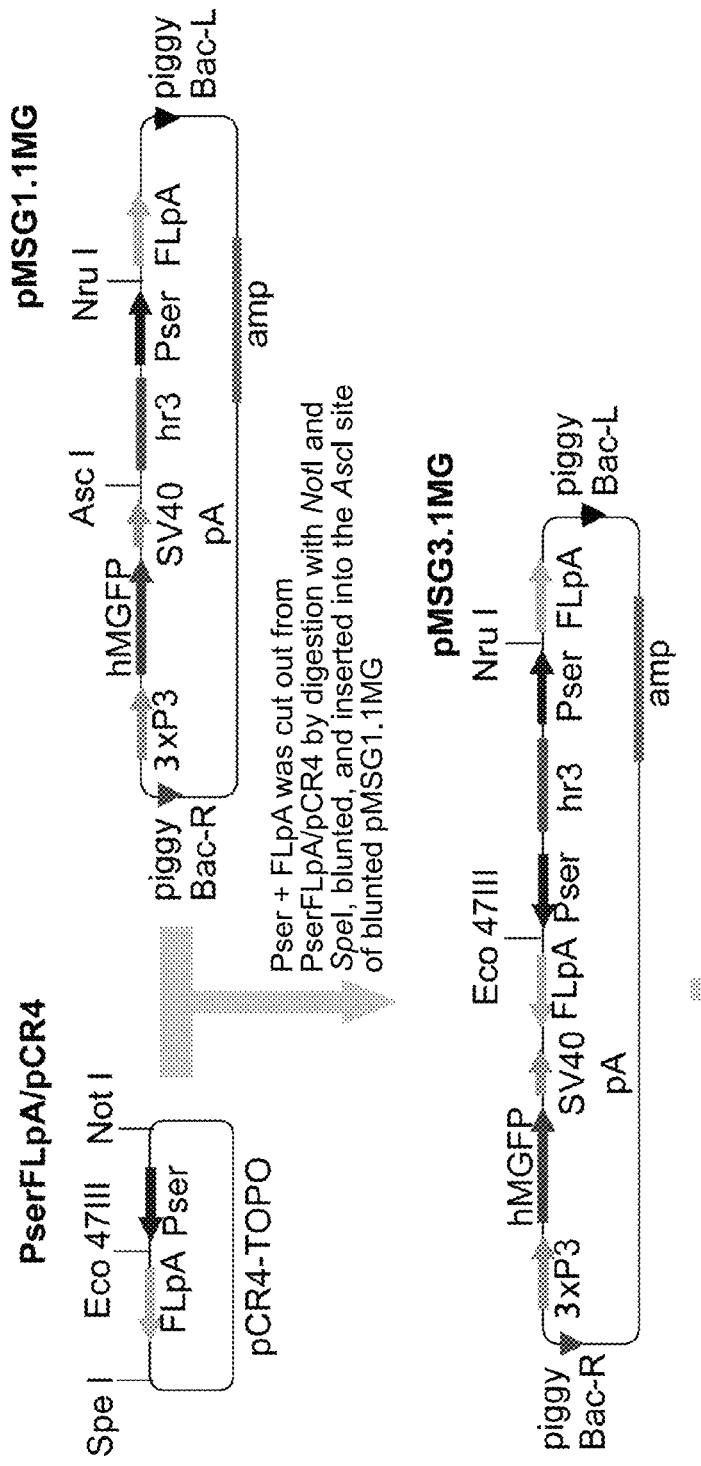
FIG. 2 shows a construction diagram for the vector used for preparation of the Aα/γ-introduced silkworm in Examples.
Figure 3:
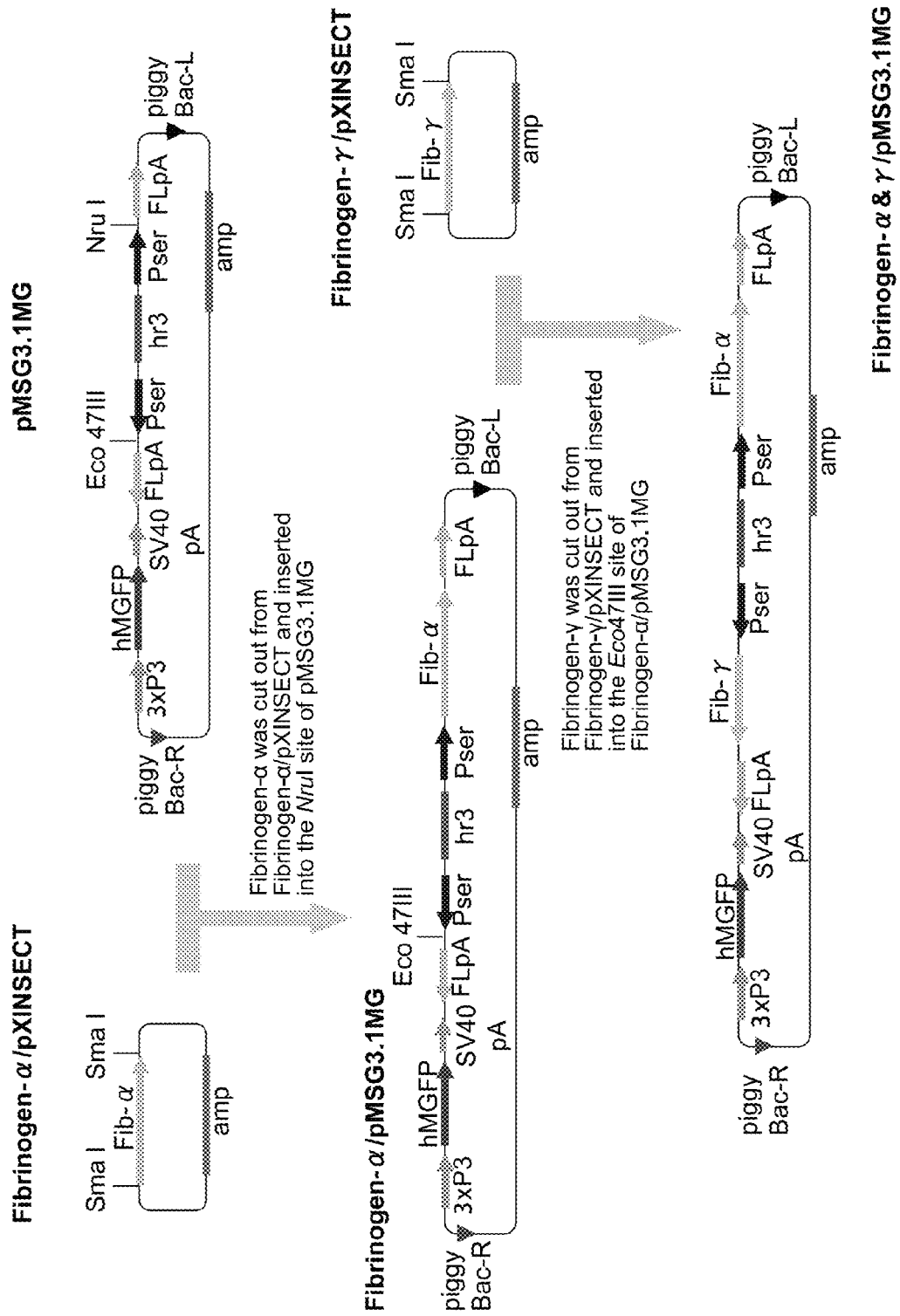
FIG. 3 shows a construction diagram for the vector used for preparation of the Aα/γ-introduced silkworm in Examples (continued from FIG. 2).

The vector construction diagrams shown in FIGS. 1 to 3 illustrate the vectors used for preparation of the transgenic silkworm in the Examples below. pMSG-1.1R and pMSG1.1MG used are known as vectors which allow a desired recombinant protein to be secreted into the sericin layer in silkworms (J Biosci Bioeng 105, 595-603 (2008); FEBS Journal 276, 5806-5820 (2009)). These vectors contain the enhancer hr3 and the sericin 1 promoter Pser, and an NruI site for insertion of a foreign gene cDNA is present between the Pser and the silkworm fibroin L-chain poly(A) addition signal FLpA (see FIG. 1 and FIG. 2). pMSG3.1MG in FIG. 3 is a vector prepared by modifying pMSG1.1MG such that two subunit genes can be introduced thereinto, and comprises the Eco47III site within the second Pser+FLpA as a site for insertion of the second subunit gene. As a marker for gene transfer, a sequence encoding a fluorescent protein (DsRed, GFP) is incorporated downstream of the promoter 3×P3 such that the sequence is functionally linked to the promoter. Since 3×P3 is a promoter that functions in eyes and nervous systems, a transgenic silkworm can be easily selected based on the presence/absence of the fluorescence from these tissues.

The thus constructed vector can be microinjected into a silkworm egg together with a transposase-expressing helper plasmid by the method specifically described in the Examples below. The helper plasmid to be used may be any one as long as it can express transposase from the plasmid in a silkworm egg, and a known plasmid such as pHA3PIG (Nat. Biotechnol. 18, 81-84 (2000)) used in the Examples below may be used as the helper plasmid. The vector and the helper plasmid are usually mixed together at a ratio of about 1:1 for use in the injection. The vector and the helper plasmid may be added to an injection buffer (e.g., a buffer comprising 0.5 mM phosphate buffer pH 7.0 and 5 mM KCl) such that each of them is contained at a concentration of about 200 μg/ml, and the resulting mixture may be injected into silkworm eggs at the preblastoderm stage, i.e. 2 to 8 hours after spawning, in a liquid volume of about 15 to 20 nl/egg.

The F0 generation hatched from the egg after the injection is crossed with the same F0 generation or with the wild-type strain to obtain F 1. When the F1 eggs before hatching or the hatched F1 larvae are irradiated with the excitation light, fluorescence from the marker fluorescent protein can be observed in the eyes and the nervous system in the eggs or larvae comprising the genes introduced thereinto, and thus such individuals can be selected. Incorporation of the subunit genes into the silkworm genome may be finally confirmed by PCR, Southern blotting and/or the like. Individuals showing sufficiently high levels of expression of the subunit proteins may be further selected as appropriate by observing the expression levels of the subunit genes in the silk gland cells or the amounts of the subunit proteins secreted into the cocoon filament by a conventional method.

In cases where three transgenic silkworm strains expressing Aα, Bβ and γ, respectively, are prepared, the transgenic silkworm of the present invention into which the three genes have been introduced can be obtained by sequential crossing of these three strains. In cases where a silkworm strain into which one gene has been introduced and a silkworm strain into which the other two genes have been introduced are prepared, the transgenic silkworm of the present invention into which the three genes have been introduced can be obtained by crossing the two strains.

The cocoon of the transgenic silkworm of the present invention comprises active fibrinogen hexamer composed of the three subunits. Formation of the hexamer can be confirmed based on its size observed by electrophoresis under a non-reducing condition. By recovering fibrinogen from the cocoon, a large amount of safe fibrinogen can be obtained without a danger of contamination with viruses etc. that can infect human. In cases where the subunit genes are expressed in the posterior silk gland to allow fibrinogen to be secreted into the fibroin layer of the cocoon filament, the fibrinogen can be recovered by dissolving the fibroin. For dissolution of the fibroin, a chaotropic salt such as lithium thiocyanate, guanidine thiocyanate or lithium bromide; a mixture of calcium chloride and ethanol; or the like is used. In cases where the subunit genes are expressed in the middle silk gland to allow fibrinogen to be secreted into the sericin layer of the cocoon filament, the fibrinogen can be easily extracted by immersing the cocoon filament in an aqueous buffer since the sericin layer is relatively soluble in water. The extraction from the cocoon filament may be carried out by immersing the cocoon as it is in an extraction liquid, or by immersing the cocoon after cutting, pulverization or the like as appropriate.

The fibrinogen secreted into the sericin layer can be extracted and recovered basically by only immersion in an aqueous buffer. Examples of especially preferred extraction conditions include extraction in a buffer containing 1 to 4 M urea, 25 to 100 mM Tris-HCl (pH 6.5 to 8.5), 0.01 to 2.0% surfactant and 0 to 0.25 M NaCl at a low temperature of about 4° C. to 10° C. for about 10 hours to 24 hours, preferably about 12 hours to 18 hours. Such a condition enables efficient extraction of fibrinogen while suppressing elution of sericin, and provides a state advantageous for the later purification steps. The urea concentration is more preferably 1 to 3 M. As a surfactant, polyoxyethylene octylphenyl ether (trade name Triton X-100), polyethylene glycol-p-octylphenyl ether (trade name NP-40), 3-[(3-cholamidopropyl)dimethylammonio]-1-propanesulfonate (trade name CHAPS) and the like may be used, and a mixture of two or more surfactants may also be used. The NaCl concentration in the buffer is preferably low, and may be not more than 0.1 M, or not more than 0.01 M.

The fibrinogen eluted into the buffer can be obtained as a concentrated fibrinogen solution by carrying out ultrafiltration and buffer exchange as appropriate, and removal of the precipitates if necessary. As described in the Examples below, when the fibrinogen recovered from the cocoon of the transgenic silkworm of the present invention in the above-described manner is mixed with thrombin and the reaction is allowed to proceed at 37° C. for 1 hour, an increase in the viscosity of the reaction liquid is observed, which confirms that the recovered fibrinogen has coagulation activity.

EXAMPLES

The present invention is described below in more detail by way of Examples.

However, the present invention is not limited to the Examples below. In the Examples below and the drawings, "Aα chain" is also simply referred to as "α chain", and "Bβ chain" is also simply referred to as "β chain".

1. Preparation of Human Fibrinogen cDNA Fragment cDNA fragments of the three subunits of fibrinogen, Aα, Bβ and γ, were amplified by PCR from a cDNA library of human liver. Replacement of the signal sequence, addition of the initiation codon ATG and addition of the UTR sequence were sequentially carried out while subcloning was carried out as appropriate, thereby preparing each subunit cDNA fragment to be inserted into an expression vector for the silkworm middle silk gland. The preparation of the cDNA fragment for each subunit is described in detail below. The PCR reaction was carried out in a volume of 50 µl using 5 units of Ex Taq or 1 unit of KOD.

(1) Obtaining Aα-Chain cDNA

From the cDNA library, an Aα-chain cDNA fragment (hereinafter referred to as Alpha) was amplified under the following reaction conditions. The first PCR product was subjected to electrophoresis in agarose gel, and the band that was assumed to correspond to Alpha was recovered and purified from the gel. The purified product was used as a template in the second PCR.

TABLE 1

| First PCR | |
|---|---|
| Enzyme | Ex Taq (TAKARA) |
| Template | cDNA Library (Plasmid DNA) Human Liver (TAKARA Code No. 9505) (200 ng) |
| Primers | alpha Bam1 F1(SEQ ID NO: 13) (10 pmoles) alpha Hind3 R1(SEQ ID NO: 14) (10 pmoles) |
| Reaction | 94° C. 5 min → (94° C. 2 min → 50° C. 2 min → 72° C. 2 min) × 25 → 72° C. 7 min → storage at 4° C. |
| Second PCR | |
| Enzyme | Ex Taq |
| Template | Purified first PCR product (10 ng) |
| Primers | alpha Bam1 F2 (SEQ ID NO: 15) (10 pmoles) alpha Hind3 R2 (SEQ ID NO: 16) (10 pmoles) |
| Reaction | 94° C. 5 min → (94° C. 2 min → 50° C. 2 min → 72° C. 2 min) × 25 → 72° C. 7 min → storage at 4° C. |

The second PCR product was subjected to agarose gel electrophoresis, and the band that was assumed to correspond to Alpha was recovered and purified from the gel, followed by insertion of the purified product into the BamHI-HindIII site of pBluescriptII SK+. The base sequence of the insert was confirmed, and the plasmid was designated pSK-alpha.

Subsequently, modification of the signal sequence of Alpha was carried out. In order to obtain a sequence wherein the 15 amino acids at the C-terminus is absent as in the mature form, a reverse primer Fibrinogen Alpha C1 was designed at the position corresponding to the position in the mature form. The first PCR product was subjected to agarose gel electrophoresis, and the band that was assumed to correspond to Alpha was recovered and purified from the gel. The purified product was used as a template in the second PCR.

TABLE 2

| First PCR | |
|---|---|
| Enzyme | KOD (TOYOBO) |
| Template | pSK-alpha (200 ng) |
| Primers | Fibrinogen Alpha N1(SEQ ID NO: 17) (10 pmoles) Fibrinogen Alpha C1(SEQ ID NO: 18) (10 pmoles) |
| Reaction | 96° C. 5 min → (96° C. 2 min → 55° C. 2 min → 72° C. 2 min) × 25 → 72° C. 7 min → storage at 4° C. |
| Second PCR | |
| Enzyme | KOD |
| Template | Purified first PCR product (10 ng) |
| Primers | Fibrinogen ATG N2 (SEQ ID NO: 19) (10 pmoles) Fibrinogen Alpha C1 (SEQ ID NO: 18) (10 pmoles) |
| Reaction | 96° C. 5 min → (96° C. 2 min → 55° C. 2 min →72° C. 2 min) × 25 → 72° C. 7 min → storage at 4° C. |

The second PCR product was subjected to agarose gel electrophoresis, and the band that was assumed to correspond to Alpha was recovered and purified from the gel. Using Ex Taq, A was added to the 3'-end of the purified second PCR product, and the product was ligated into pCR2.1-TOPO. The base sequence of the insert was confirmed, and the plasmid was designated pCR-ATGalpha.

Subsequently, addition of a UTR sequence was carried out as follows. The first PCR product was subjected to agarose gel electrophoresis, and the band that was assumed to correspond to Alpha was recovered and purified from the gel. The purified product was used as a template in the second PCR.

TABLE 3

| First PCR | |
|---|---|
| Enzyme | KOD |
| Template | pCR-ATGalpha (200 ng) |
| Primers | Fibrinogen UTR N3 (SEQ ID NO: 20) (10 pmoles) Fibrinogen Alpha C1 (SEQ ID NO: 18) (10 pmoles) |
| Reaction | 96° C. 5 min → (96° C. 2 min → 55° C. 2 min → 72° C. 2 min) × 25 → 72° C. 7 min → storage at 4° C. |
| Second PCR | |
| Enzyme | KOD |
| Template | Purified first PCR product (10 ng) |
| Primers | Fibrinogen UTR N4 (SEQ ID NO: 21) (10 pmoles) Fibrinogen Alpha C1 (SEQ ID NO: 18) (10 pmoles) |
| Reaction | 96° C. 5 min → (96° C. 2 min → 55° C. 2 min → 72° C. 2 min) × 25 → 72° C. 7 min → storage at 4° C. |

The second PCR product was subjected to agarose gel electrophoresis, and the band that was assumed to correspond to Alpha was recovered and purified from the gel. This purified fragment was ligated into pENTR/D-TOPO, which was a vector for incorporation into the silkworm expression vector. The base sequence of the insert was confirmed, and the plasmid was designated pENTR-UTRalpha.

(2) Obtaining Bβ-Chain cDNA

From the cDNA library, a Bβ-chain cDNA fragment (hereinafter referred to as Beta) was amplified under the following reaction conditions. The first PCR product was subjected to agarose gel electrophoresis, and the band that was assumed to correspond to Beta was recovered and purified from the gel. The purified product was used as a template in the second PCR.

TABLE 4

First PCR

| Enzyme | Ex Taq |
|---|---|
| Template | cDNA Library (Plasmid DNA) Human Liver (TAKARA Code No. 9505) (200 ng) |
| Primers | beta EcoR1 F1(SEQ ID NO: 22) (10 pmoles) |
| | beta Xho1 R1(SEQ ID NO: 23) (10 pmoles) |
| Reaction | 94° C. 5 min → (94° C. 2 min → 50° C. 2 min → 72° C. 2 min) × 25 → 72° C. 7 min → storage at 4° C. |

Second PCR

| Enzyme | Ex Taq |
|---|---|
| Template | Purified first PCR product (10 ng) |
| Primers | beta EcoR1 F2 (SEQ ID NO: 24) (10 pmoles) |
| | beta Xho1 R2 (SEQ ID NO: 25) (10 pmoles) |
| Reaction | 94° C. 5 min → (94° C. 2 min → 50° C. 2 min → 72° C. 2 min) × 25 → 72° C. 7 min → storage at 4° C. |

The second PCR product was subjected to agarose gel electrophoresis, and the band that was assumed to correspond to Beta was recovered and purified from the gel. The purified product was inserted into the EcoRI-XhoI site of pBluescriptll SK+. The base sequence of the insert was confirmed, and the plasmid was designated pSK-beta.

Subsequently, modification of the signal sequence of Beta was carried out. The first PCR product was subjected to agarose gel electrophoresis, and the band that was assumed to correspond to Beta was recovered and purified from the gel. The purified product was used as a template in the second PCR.

TABLE 5

First PCR

| Enzyme | KOD |
|---|---|
| Template | pSK-beta (200 ng) |
| Primers | Beta-ATG N2 (SEQ ID NO: 26) (10 pmoles) |
| | Beta-C (SEQ ID NO: 27) (10 pmoles) |
| Reaction | 96° C. 5 min → (96° C. 2 min → 55° C. 2 min → 72° C. 2 min) × 25 → 72° C. 7 min → storage at 4° C. |

Second PCR

| Enzyme | KOD |
|---|---|
| Template | Purified first PCR product (10 ng) |
| Primers | Beta-ATG N (SEQ ID NO: 28) (10 pmoles) |
| | Beta-C (SEQ ID NO: 27) (10 pmoles) |
| Reaction | 96° C. 5 min → (96° C. 2 min → 55° C. 2 min →72° C. 2 min) × 25 → 72° C. 7 min → storage at 4° C. |

The second PCR product was subjected to agarose gel electrophoresis, and the band that was assumed to correspond to Beta was recovered from the gel. Using Ex Taq, A was added to the 3'-end of the purified second PCR product, and the product was ligated into pCR2.1-TOPO. The base sequence of the insert was confirmed, and the plasmid was designated pCR-ATGbetat.

Subsequently, addition of a UTR sequence was carried out as follows. The first PCR product was subjected to agarose gel electrophoresis, and the band that was assumed to correspond to Beta was recovered and purified from the gel. The purified product was used as a template in the second PCR.

TABLE 6

First PCR

| Enzyme | KOD |
|---|---|
| Template | pCR-ATGbetat (200 ng) |
| Primers | Fibrinogen UTR N3 (SEQ ID NO: 20) (10 pmoles) |
| | Beta-C (SEQ ID NO: 27) (10 pmoles) |
| Reaction | 96° C. 5 min → (96° C. 2 min → 55° C. 2 min → 72° C. 2 min) × 25 → 72° C. 7 min → storage at 4° C. |

Second PCR

| Enzyme | KOD |
|---|---|
| Template | Purified first PCR product (10 ng) |
| Primers | Fibrinogen UTR N4 (SEQ ID NO: 21) (10 pmoles) |
| | Beta-C (SEQ ID NO: 27) (10 pmoles) |
| Reaction | 96° C. 5 min → (96° C. 2 min → 55° C. 2 min → 72° C. 2 min) × 25 → 72° C. 7 min → storage at 4° C. |

The second PCR product was subjected to agarose gel electrophoresis, and the band that was assumed to correspond to Beta was recovered and purified from the gel. This purified fragment was ligated into pENTR/D-TOPO, which was a vector for incorporation into the silkworm expression vector. The base sequence of the insert was confirmed, and the plasmid was designated pENTR-UTRbeta.

(3) Obtaining γ-Chain cDNA

From the cDNA library, a γ-chain cDNA fragment (hereinafter referred to as Gamma) was amplified under the following reaction conditions. The first PCR product was subjected to agarose gel electrophoresis, and the band that was assumed to correspond to Gamma was recovered and purified from the gel. The purified product was used as a template in the second PCR.

TABLE 7

First PCR

| Enzyme | Ex Taq |
|---|---|
| Template | cDNA Library (Plasmid DNA) Human Liver (TAKARA Code No. 9505) (200 ng) |
| Primers | gamma EcoR1 F1 (SEQ ID NO: 29) (10 pmoles) |
| | gamma Hind3 R1 (SEQ ID NO: 30) (10 pmoles) |
| Reaction | 94° C. 5 min → (94° C. 2 min → 50° C. 2 min → 72° C. 2 min) × 25 → 72° C. 7 min → storage at 4° C. |

Second PCR

| Enzyme | Ex Taq |
|---|---|
| Template | Purified first PCR product (10 ng) |
| Primers | gamma EcoR1 F2 (SEQ ID NO: 31) (10 pmoles) |
| | gamma Hind3 R2 (SEQ ID NO: 32) (10 pmoles) |
| Reaction | 94° C. 5 min → (94° C. 2 min → 50° C. 2 min → 72° C. 2 min) × 25 → 72° C. 7 min → storage at 4° C. |

The second PCR product was subjected to agarose gel electrophoresis, and the band that was assumed to correspond to Gamma was recovered and purified from the gel, followed by insertion of the purified product into the EcoRI-HindIII site of pBluescriptII SK+. The base sequence of the insert was confirmed, and the plasmid was designated pSK-gamma.

Subsequently, modification of the signal sequence of Gamma was carried out. The first PCR product was subjected to agarose gel electrophoresis, and the band that was assumed to correspond to Gamma was recovered and purified from the gel. The purified product was used as a template in the second PCR.

TABLE 8

| | First PCR |
|---|---|
| Enzyme | KOD |
| Template | pSK-gamma (200 ng) |
| Primers | Fibrinogen gamma N1 (SEQ ID NO: 33) (10 pmoles) |
| | Fibrinogen gamma C1 (SEQ ID NO: 34) (10 pmoles) |
| Reaction | 96° C. 5 min → (96° C. 2 min → 55° C. 2 min → |
| | 72° C. 2 min) × 25 → 72° C. 7 min → storage at 4° C. |

| | Second PCR |
|---|---|
| Enzyme | KOD |
| Template | Purified first PCR product (10 ng) |
| Primers | Fibrinogen ATG N2 (SEQ ID NO: 19) (10 pmoles) |
| | Fibrinogen gamma C1 (SEQ ID NO: 34) (10 pmoles) |
| Reaction | 96° C. 5 min → (96° C. 2 min → 55° C. 2 min → |
| | 72° C. 2 min) × 25→ 72° C. 7 min → storage at 4° C. |

The second PCR product was subjected to agarose gel electrophoresis, and the band that was assumed to correspond to Gamma was recovered and purified from the gel. Using Ex Taq, A was added to the 3'-end of the purified second PCR product, and the product was ligated into pCR2.1-TOPO. The base sequence of the insert was confirmed, and the plasmid was designated pCR-ATGgamma.

Subsequently, addition of a UTR sequence was carried out as follows. The first PCR product was subjected to agarose gel electrophoresis, and the band that was assumed to correspond to Gamma was recovered and purified from the gel. The purified product was used as a template in the second PCR.

TABLE 9

| | First PCR |
|---|---|
| Enzyme | KOD |
| Template | pCR-ATGgamma (200 ng) |
| Primers | Fibrinogen UTR N3 (SEQ ID NO: 20) (10 pmoles) |
| | Fibrinogen gamma C1 (SEQ ID NO: 34) (10 pmoles) |
| Reaction | 96° C. 5 min → (96° C. 2 min → 55° C. 2 min → |
| | 72° C. 2 min) × 25 → 72° C. 7 min → storage at 4° C. |

| | Second PCR |
|---|---|
| Enzyme | KOD |
| Template | Purified first PCR product (10 ng) |
| Primers | Fibrinogen UTR N4 (SEQ ID NO: 21) (10 pmoles) |
| | Fibrinogen gamma C1 (SEQ ID NO: 34) (10 pmoles) |
| Reaction | 96° C. 5 min → (96° C. 2 min → 55° C. 2 min → |
| | 72° C. 2 min) × 25 → 72° C. 7 min → storage at 4° C. |

The second PCR product was subjected to agarose gel electrophoresis, and the band that was assumed to correspond to Gamma was recovered and purified from the gel. This purified fragment was ligated into pENTR/D-TOPO, which was a vector for incorporation into the silkworm expression vector. The base sequence of the insert was confirmed, and the plasmid was designated pENTR-UTR-gamma.

2. Construction of Human Fibrinogen Expression Vector

Using the GATEWAY system provided by Invitrogen, the fragment cloned in the entry vector pENTR/D-TOPO was subcloned into pXINSECT-DEST38. The inserted fragment was cut out from the resulting plasmid, and then inserted into a known expression vector for the silkworm middle silk gland. Two vectors, that is, a vector that expressed the Bβ chain and a vector that expressed the Aα chain and the γ chain were prepared. The details are described below.

(1) Bβ Chain-Expressing Vector Fibrinogen-β/pMSG1.1R (See FIG. 1)

From pENTR-UTRbeta prepared as described above, the inserted gene was subcloned into pXINSECT-DEST38 using the GATEWAY system. The Fibrinogen-β cDNA was cut out from the obtained Fibrinogen-β/pXINSECT by SmaI digestion, and then inserted into the NruI site of pMSG1.1R, a known vector for transformation of silkworms (J Biosci Bioeng 105, 595-603 (2008)), to complete construction of Fibrinogen-β/pMSG1.1R for transformation of silkworms (FIG. 1). The pMSG1.1R vector allows an inserted gene to be expressed in the middle silk gland under the control of the sericin 1 gene promoter Pser1, which functions in the middle silk gland cells. The vector comprises baculovirus-derived hr3 as an enhancer, and as a marker for the expression of transgene, a red fluorescent protein gene DsRed under the control of the promoter 3xP3, which functions in the eyes and the nervous system of a silkworm.

(2) Aα-Chain/γ-Chain-Expressing Vector Fibrinogen-α&γ/pMSG-MG (See FIGS. 2 and 3)

From pENTR-UTRalpha and pENTR-UTRgamma prepared as described above, each inserted gene was subcloned into pXINSECT-DEST38 using the GATYEWAY system (Fibrinogen-α/pXINSECT and Fibrinogen-γ/pXINSECT).

On the other hand, a gene transfer vector pMSG3.1MG for expression of the two kinds of genes was constructed as described below from pMSG1.1MG, a known vector for transformation of silkworms (FEBS Journal 276, 5806-5820 (2009)) (FIG. 2). pMSG1.1MG is a vector prepared from the above-described pMSG1.1R by replacing the transgene expression marker DsRed with a green fluorescent protein gene hMGFP.

From pCR4-TOPO vector (PserFLpA/pCR4) comprising a sequence composed of the sericin 1 promoter, an Eco47III restriction site and a fibroin L-chain poly(A) addition signal inserted therein, the insert DNA was cut out with NotI and SpeI whose sites were originally contained in the vector, and the obtained insert DNA was blunted. Thereafter, pMSG1.1MG was digested with AscI (the AscI site is positioned between the SV40 poly(A) addition signal and hr3) and blunted, and the blunted insert DNA was inserted thereinto. By the above operation, construction of pMSG3.1MG was completed (FIG. 2).

The Fibrinogen-α cDNA was cut out from Fibrinogen-α/pXINSECT by SmaI digestion, and the cDNA was inserted into the NruI site of the pMSG3.1MG vector prepared as described above to obtain Fibrinogen-α/pMSG3.1MG. The Fibrinogen-γ cDNA was cut out from Fibrinogen-γ/pXINSECT, and the cDNA was inserted into the Eco47III site of Fibrinogen-α/pMSG3.1MG, thereby completing construction of Fibrinogen-α&γ/pMSG3.1MG (FIG. 3).

3. Preparation of Transgenic Silkworm (1) Preparation of Bβ-Introduced Silkworm

The gene transfer vector constructed as described above, Fibrinogen-β/pMSG1.1 R, was purified by cesium chloride ultracentrifugation, and mixed with a helper plasmid pHA3PIG (Nat. Biotechnol. 18, 81-84 (2000)) such that the plasmid ratio was 1:1. The resulting mixture was concentrated by ethanol precipitation, and dissolved in an injection buffer (0.5 mM phosphate buffer pH 7.0, 5 mM KCl) such that the concentration of each of the gene transfer vector and pHA3PIG became 200 μg/ml to obtain a DNA solution for injection into eggs. This DNA solution was microinjected into silkworm eggs (silkworm embryos) at the preblastoderm stage, i.e. 2 to 8 hours after spawning, in a liquid amount of about 15 to 20 nl/egg, and the eggs were incubated at 25° C. From a total of 3,032 eggs subjected to the injection, 600 eggs were hatched. By crossing reproductive adults obtained therefrom, 112 groups of F1 egg masses were obtained. F1 egg masses on Day 5 to 6 after spawning were observed under a fluorescence stereoscopic microscope to select eggs in which expression of the marker gene, i.e. red fluorescence from the eyes and the nervous system, could be seen. Seven groups of egg masses containing eggs of Bβ-expressing silkworms were obtained. These eggs were allowed to hatch and the larvae were grown. As a result, transgenic silkworms originated from a plurality of egg masses could be normally grown to be reproductive adults. The adults were crossed with wild-type silkworms to obtain 6 strains of Bβ-introduced silkworms.

(2) Preparation of Aα/γ-Introduced Silkworm

In the same manner as described above, the gene transfer vector Fibrinogen-α&γ/pMSG3.1MG was purified, and microinjected into silkworm eggs together with the helper plasmid. From a total of 3,336 eggs subjected to the injection, 1,050 eggs were hatched. By crossing reproductive adults obtained therefrom, 233 groups of F1 egg masses were obtained. Eggs were selected based on green fluorescence from the eyes and the nervous system, and 17 groups of egg masses containing eggs of Aα/γ-expressing silkworms were obtained. Normally grown adults were crossed with wild-type silkworms to obtain 14 strains of Aα/γ-introduced silkworms.

(3) Confirmation of Expression of Fibrinogen Subunits

Figure 4:
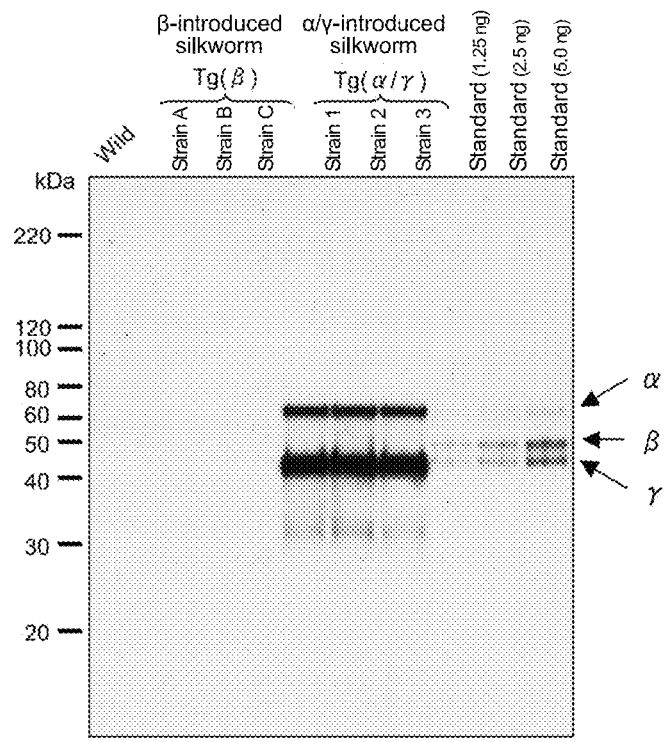
FIG. 4 shows an example of the results of detection, by Western blotting, of the subunit proteins in the cocoon filaments of the Bβ-introduced silkworm and the Aα/γ-introduced silkworm prepared in Examples.

The Bβ-introduced silkworm strain and the Aα/γ-introduced silkworm strain obtained as described above were investigated for secretion of the proteins of interest into their cocoons by Western blotting. The cocoons were cut and immersed in a buffer containing 8 M urea (8 M urea, 50 mM Tris buffer, pH 8.0), and heated at 80° C. for 5 minutes, followed by centrifugation to obtain a supernatant, which was then subjected to Western blotting. A part of the results is shown in FIG. 4. Secretion of both Aα chain and γ chain into the cocoons could be confirmed in the Aα/γ-introduced silkworms. However, the Bβ chain could not be detected in the cocoons of the Bβ-introduced silkworms.

Figure 5:
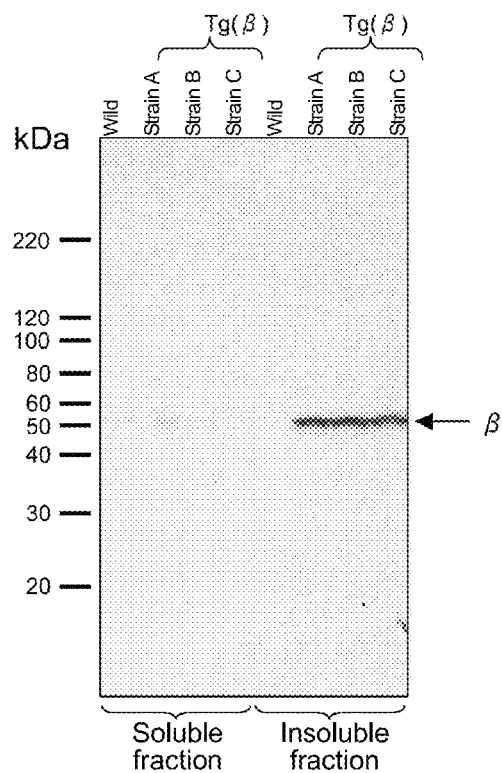
FIG. 5 shows an example of the results of investigation, by Western blotting, of expression of the Bβ chain in the silk glands of the Bβ-introduced silkworm prepared in Examples.

In order to investigate whether the Bβ chain was expressed as a protein in the silk gland cells, expression analysis was carried out using silk glands of fifth instar larvae. The silk glands were collected from fifth instar larvae of wild-type and Bβ-introduced silkworms, and subjected to extraction with 1×TBS. After centrifugation, the resulting supernatant was obtained as a soluble fraction. The precipitate was further subjected to extraction with 1×SDS-PAGE sample buffer to obtain an insoluble fraction. The fractions were electrophoresed and Western blotting was carried out to find that the signal for the Bβ chain was detected in the insoluble fraction (FIG. 5). Thus, it could be confirmed that, in Bβ-introduced silkworms, the Bβ chain was normally synthesized but stayed inside the silk gland cells.

(4) Preparation of Aα/Bβ/γ-Introduced Silkworm

Figure 6:
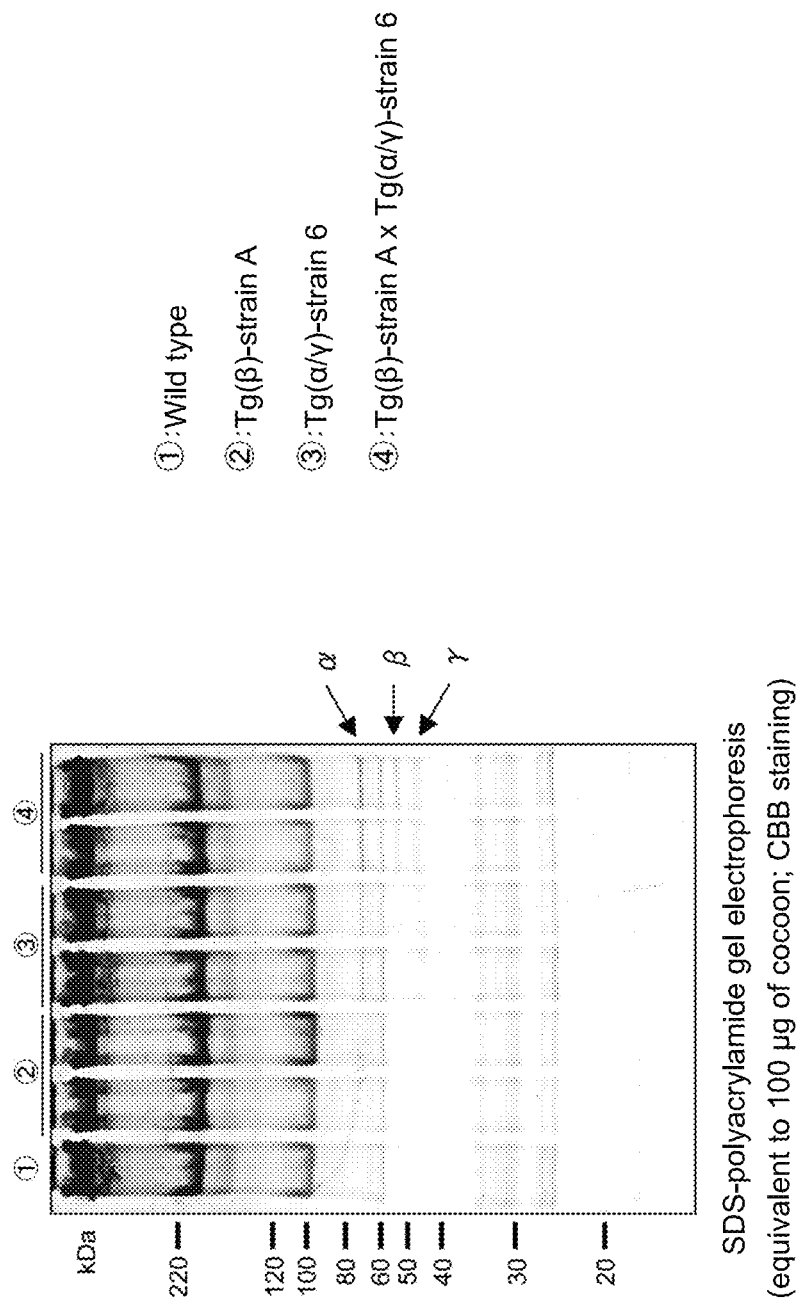
FIG. 6 shows CBB (Coomassie brilliant blue) staining of electrophoresed proteins contained in the cocoon filament of the transgenic silkworms prepared in Examples.

Bβ-introduced silkworms, in which secretion of the Bβ chain into the cocoons could not be observed, were crossed with Aα/γ-introduced silkworms, in which secretion of the Aα chain and the γ chain into the cocoons could be observed, to obtain a plurality of strains of Aα/Bβ/γ-introduced silkworms. These plurality of strains of silkworms were subjected to irradiation with the excitation light at the egg or larva stage to confirm that yellow fluorescence as a result of combination of red fluorescence and green fluorescence could be observed. The proteins contained in the cocoons of these silkworms were extracted in the same manner as described above, and subjected to SDS-polyacrylamide gel electrophoresis, followed by observation by CBB staining. As a result, a clear band could be detected for all of the Aα chain, Bβ chain and γ chain (FIG. 6).

4. Use of Transcription Factor for Increasing Expression Level of Fibrinogen

It is known that the activity of the sericin promoter largely increases in cases where the sericin promoter is used in combination with hr3, which is an enhancer derived from a baculovirus (BmNPV), and the IE1 gene, which is a transactivator similarly derived from BmNPV (see JP 4271122 B). This technique has been utilized for expression of a recombinant protein in silkworms, and a transgenic silkworm strain that expresses IE1 protein in the middle silk gland is known (FEBS Journal 276, 5806-5820 (2009), Biotechnol Bioeng 106, 860-870 (2010)). Using the known IE1-expressing silkworm, we attempted to enhance the expression level of the transgenes in the Aα/Bβ/γ-introduced silkworm.

Figure 7:
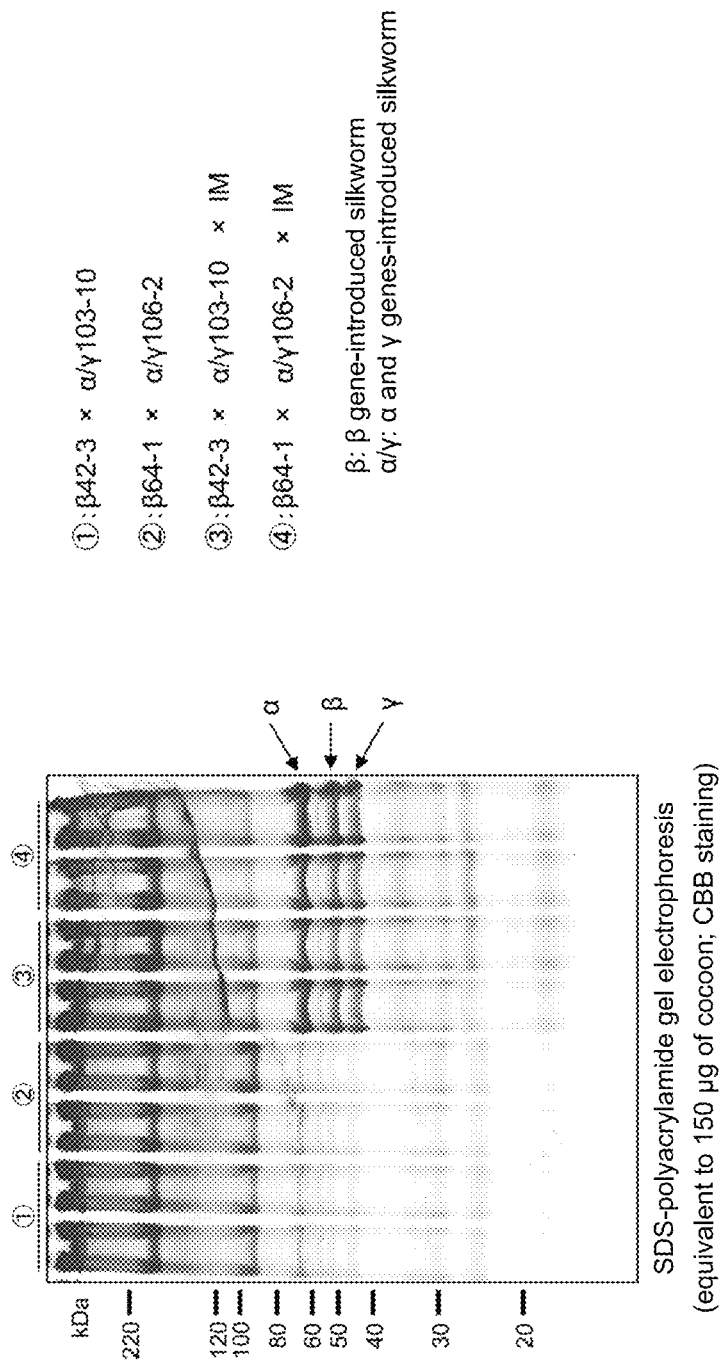
FIG. 7 is an electrophoretic profile showing an increased amount of each subunit of fibrinogen accumulated in the cocoons of transgenic silkworms into which transactivator IE1 has been introduced.

The IM1 silkworm is a silkworm into which IE1 has been introduced under the control of the sericin 1 promoter, and the silkworm shows high expression of transcription factor IE1 (Biotechnol Bioeng 106, 860-870 (2010)). Aα/Bβ/γ-introduced silkworms prepared as described above were crossed with IM1 silkworms to obtain Aα/Bβ/γ×IM silkworms, and the cocoons of the Aα/Bβ/γ×IM silkworms were obtained. The expression level of each subunit (content of each subunit in the cocoon filament) in the obtained cocoons was investigated. The results showed that the expression level of fibrinogen largely increased, but the cocoon weight decreased to about 30 to 40% (Table 10 and FIG. 7).

TABLE 10

| Silkworm strain | Cocoon weight |
| --- | --- |
| Wild type | 89.6 mg |
| β42-3 × α/γ103-10 | 84.2 mg |
| β64-1 × α/γ106-2 | 78.8 mg |
| β42-3 × α/γ103-10 × IM | 34.0 mg |
| β64-1 × α/γ106-2 × IM | 24.7 mg |

Figure 8:
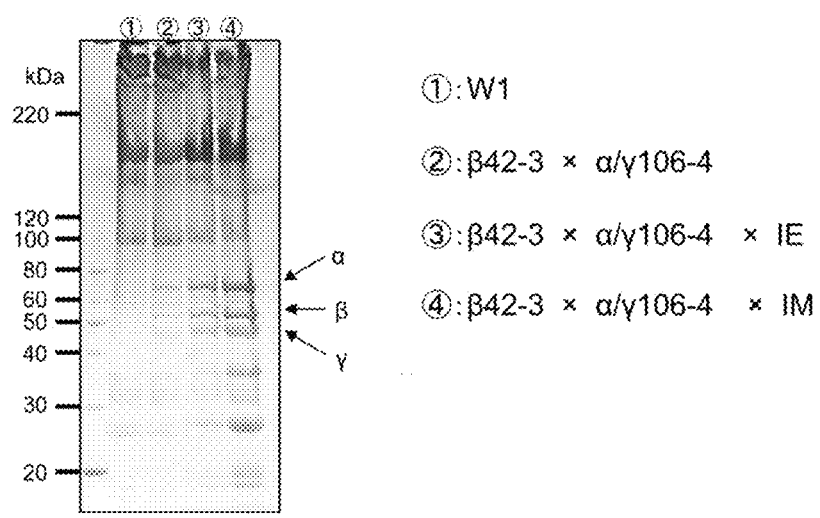
FIG. 8 is an electrophoretic profile showing influence of differences in the expression level of transactivator IE1 on the expression levels (amounts accumulated in the cocoon filament) of the subunits.

The IE1 silkworm is a strain showing a lower expression level of IE1 than the IM1 silkworm (FEBS Journal 276, 5806-5820 (2009)). Crossing with IE1 silkworms was carried out to obtain Aα/Bβ/γ×IE silkworms, and the cocoons of the Aα/Bβ/γ×IE silkworms were obtained. The expression level of each subunit (content of each subunit in the cocoon filament) in the obtained cocoons and the cocoon weight were investigated. Decrease in the cocoon weight could be avoided. The expression level of fibrinogen was higher than that in Aα/Bβ/γ silkworms, but lower than that in Aα/Bβ/γ×IM silkworms (Table 11 and FIG. 8).

TABLE 11

| Silkworm strain | Cocoon weight |
| --- | --- |
| Wild type | 89.6 mg |
| β42-3 × α/γ106-4 | 86.4 mg |
| β42-3 × α/γ106-4 × IE | 68.2 mg |
| β42-3 × α/γ106-4 × IM | 34.0 mg |

When comparing Aα/Bβ/γ×IM silkworms and Aα/Bβ/γ×IE silkworms, the former Aα/Bβ/γ×IM silkworms were found to show higher production of fibrinogen in terms of the total production per cocoon. Thus, crossing with an IM1 silkworm, which highly expresses the transactivator, is advantageous for production of fibrinogen.

5. Investigation of Conditions for Extraction of Recombinant Fibrinogen from Cocoon In order to efficiently extract fibrinogen from the cocoons of Aα/Bβ/γ-introduced silkworms, extraction conditions were investigated.

Figure 9:
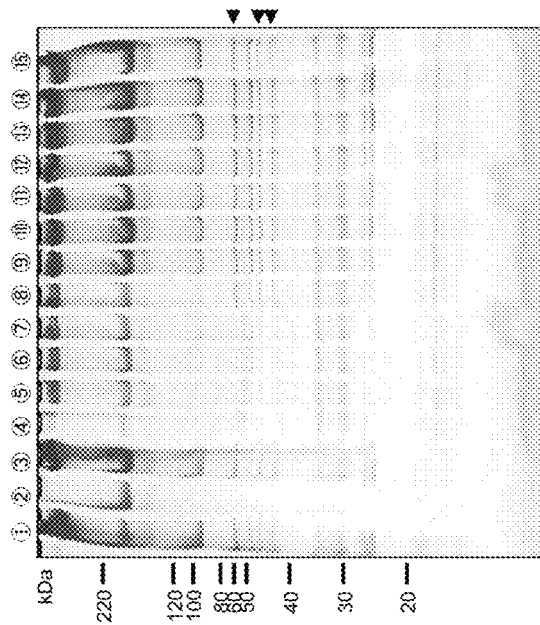
FIG. 9 shows the results of investigation on the conditions for extraction of fibrinogen from cocoon filaments using the cocoons of transgenic silkworms into which transactivator IE1 has not been introduced.

Using the cocoons of Aα/Bβ/γ-introduced silkworms into which the transactivator had not been introduced, the conditions for extraction of fibrinogen were investigated. The cocoons were cut and immersed in a buffer to perform extraction treatment. Since extraction with PBS was difficult, buffers with various compositions containing NaCl, a surfactant and/or the like were used for the investigation as shown in FIG. 9. It is desirable to carry out the extraction while avoiding extraction of sericin as much as possible in consideration of subsequent purification steps, and it is desirable to make the urea concentration lower in order to suppress denaturation. In view of these, it was considered that the most preferred condition is one described as No. 8 (2 M urea, 50 mM Tris-HCl (pH 7.5), 1% Triton X-100; extraction at 4° C. for 16 hours) in FIG. 9.

Figure 10:
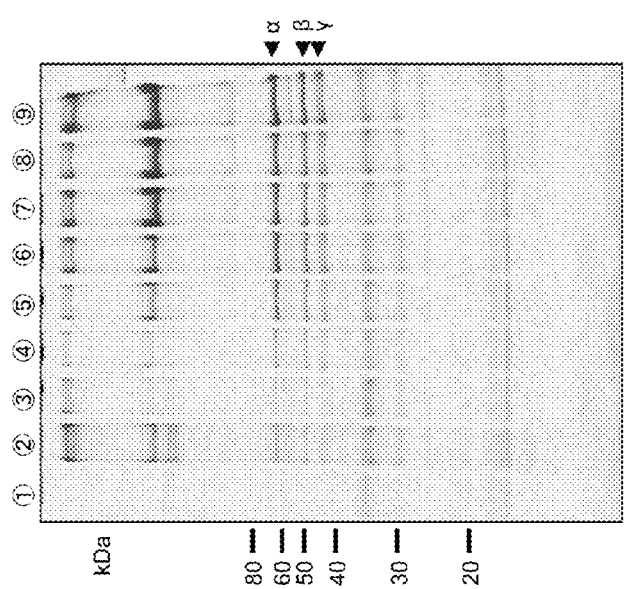
FIG. 10 shows the results of investigation on the conditions for extraction of fibrinogen from cocoon filaments using the cocoons of transgenic sawmills into which transactivator IE1 has been introduced.

Using the cocoons of Aα/Bβ/γ×IM silkworms into which the transactivator had been introduced, the conditions for extraction of fibrinogen were investigated as shown in FIG. 10 (extraction was carried out at 4° C. for 16 hours in all cases). Since the expression level of fibrinogen was higher than that in the Aα/Bβ/γ silkworms used in the above-described investigation, fibrinogen could be efficiently extracted under milder conditions, and the extraction could be sufficiently carried out even when the concentration of Triton X-100 was lowered to 0.1%.

The cocoons of Aα/Bβ/δ×IM silkworms were subjected to extraction with 6 M urea, 50 mM Tris-HCl (pH 7.5), and the extracts were electrophoresed under non-reducing conditions (without 2-mercaptoethanol). Although a clear band could not be formed due to the large molecular weight of the protein, it was considered from its size that the protein was a hexamer (data not shown).

6. Confirmation of Coagulation Activity of Fibrinogen

Whether human fibrinogen produced in a silkworm could react with thrombin to cause coagulation (to form fibrin clot) was investigated.

Cocoons of β42-3×α/γ106-2×IM were subjected to extraction with 2 M urea, 50 mM Tris-HCl (pH7.5) and 0.1% Triton X-100 at 4° C. overnight. By ultrafiltration (Amicon Ultra-15 10,000 NMWL, Millipore), the extract was concentrated from 15 ml to 400 µl. Subsequently, 15 ml of 100 mM Tris-HCl (pH8.0), 200 mM NaCl, 500 nM $CaCl_2$ was added thereto, and the resulting mixture was concentrated again to 400 µl (buffer exchange). At this stage, a part of the proteins was insolubilized to cause precipitation. After removal of the precipitate, thrombin (Calbiochem) was added to the obtained liquid to a final concentration of 10 U/ml, and the resulting mixture was incubated at 37° C. for 1 hour. As a result, viscosity of the liquid increased to an extent where, when the liquid was sucked into a pipette, the liquid hardly dropped from the tip of the pipette. Thus, the coagulation activity of the fibrinogen produced by the silkworm could be confirmed.

---

The invention claimed is:

1. A transgenic silkworm whose genome comprises cDNAs of human fibrinogen subunits Aα, Bβ and γ,
    wherein each of said cDNAs comprises a 5'-UTR sequence and is functionally linked to a promoter of a sericin gene, and a region encoding an original signal peptide in each of said cDNAs is replaced with a region encoding human calreticulin signal peptide, and cDNA of the subunit Aα lacks a region encoding 15 amino acids at a C-terminus; and
    wherein said cDNAs encode said human fibrinogen subunits in middle silk glands of the transgenic silkworm, and said transgenic silkworm produces human fibrinogen in a sericin layer of the cocoon filament, said human fibrinogen having coagulation activity.

2. The transgenic silkworm according to claim 1, wherein the Aα, Bβ and γ cDNAs have been introduced in combination with an enhancer.

3. The transgenic silkworm according to claim 2, wherein said enhancer is hr3 derived from a baculovirus.

4. The transgenic silkworm according to claim 1, wherein the Aα, Bβ and γ cDNAs have been introduced in combination with a transactivator.

5. The transgenic silkworm according to claim 4, wherein said transactivator is transcription factor IE1 derived from a baculovirus.

6. A method for producing a transgenic silkworm that produces human fibrinogen having coagulation activity in the cocoon filament, said method comprising:
    a) preparing a first silkworm by introducing a vector comprising a cDNA encoding Bβ subunit of fibrinogen into one or more silkworm eggs, wherein said cDNA comprises a 5'-UTR sequence and is functionally linked to a promoter of a sericin gene, wherein a region encoding an original signal peptide in said cDNA is replaced with a region encoding human calreticulin signal peptide,
    b) preparing a second silkworm by introducing a second vector comprising cDNAs encoding Aα and γ subunits of human fibrinogen into one or more silkworm eggs, wherein each of said cDNAs comprises a 5'-UTR sequence and is functionally linked to a promoter of a sericin gene, wherein a region encoding an original signal peptide in each of said cDNAs is replaced with a region encoding human calreticulin signal peptide, and wherein DNA of the subunit Aα lacks a region encoding the 15 amino acids at the C-terminus,
    c) crossing the first silkworm with the second silkworm to obtain a transgenic silkworm that expresses the Aα, Bβ and γ subunits in its middle silk gland cells and produces fibrinogen having coagulation activity in the cocoon filament.

7. The method according to claim 6, wherein the first vector and the second vector comprise an enhancer.

8. The method according to claim 7, wherein said enhancer is hr3 derived from a baculovirus.

9. The method according to claim 6, wherein the step a) and the step b) further comprise introducing a transactivator to said one or more silkworm eggs.

10. The method according to claim 9, wherein said transactivator is transcription factor IE1 derived from a baculovirus.

11. The transgenic silkworm according to claim 2, wherein the Aα, Bβ and γ cDNAs have been introduced in combination with a transactivator.

* * * * *